(12) United States Patent
Fisher et al.

(10) Patent No.: US 7,468,273 B2
(45) Date of Patent: *Dec. 23, 2008

(54) CANINE GHRH GENE, POLYPEPTIDES AND METHODS OF USE

(75) Inventors: Laurent Bernard Fisher, Sainte Foy les Lyon (FR); Nathalie Michele Cachet, Sainte Foy les Lyon (FR); Simona Barzu-Le-Roux, Lentilly (FR)

(73) Assignee: Meial Limited, Duluth, GA (US)

( * ) Notice: Subject to any disclaimer, the term of this patent is extended or adjusted under 35 U.S.C. 154(b) by 275 days.

This patent is subject to a terminal disclaimer.

(21) Appl. No.: 11/015,461

(22) Filed: Dec. 17, 2004

(65) Prior Publication Data

US 2005/0164946 A1 Jul. 28, 2005

Related U.S. Application Data

(63) Continuation-in-part of application No. 10/838,122, filed on May 3, 2004.

(60) Provisional application No. 60/467,405, filed on May 1, 2003.

(51) Int. Cl.
*C12N 15/63* (2006.01)
*A61K 48/00* (2006.01)

(52) U.S. Cl. .................. 435/320.1; 514/44

(58) Field of Classification Search .......... 514/44; 435/320.1

See application file for complete search history.

(56) References Cited

U.S. PATENT DOCUMENTS 7,351,815 B2    4/2008   Fisher et al.

FOREIGN PATENT DOCUMENTS

| EP | 0137689 | 4/1985 |
|---|---|---|
| EP | 0459747 | 12/1991 |
| EP | 1052286 | 11/2000 |
| WO | WO 2004/108761 | 12/2004 |

OTHER PUBLICATIONS

Binley et al, (Blood, 100(7): 2406-2413, 2002.*
Draghia-Akli et al, (FASEB, 17(3): 526-8, 2003.*
Draghia-Akli et al, (Molecular Therapy, 6(6): 830-836, 2002.*
Ahmed et al, (Journal of Endocrinology, 172: 117-125, 2002.*
Draghia-Akli, E. et al., Effects of Plasmid-mediated Growth Hormone-releasing Hormone in Severly Debilitated Dogs with Cancer:—*Molecular Therapy*, Dec. 2002, vol. 6, No. 6, pp. 830-836.
Gonzalez-Crespo, S., et al., "Expression of the Rat Growth Hormone-releasing Hormone Gene in Placenta is Directed by an Alternative Promper"—*Proceedings of the National Academy of Sciences*, USA, Oct. 1991; vol. 88, No. 19, pp. 8749-8753.
Gomberg-Maitland, M., et al., "Recombinant Growth Hormone: A New Cardiovascular Drug Therapy"—*American Heart Journal*, Dec. 1996, vol. 132, No. 6, pp. 1244-1262.
Bartlett, et al., "Growth Hormone, Insulin, and Somatostatin Therapy of Cancer Cachexia"—Cancer, 1994. vol. 73, pp. 1499-1504.
Bartlett, et al., "Effect of Growth Hormone and Protein Intake on tumor Growth and Host Cachexia" Surgery, 1995, vol. 117 pp. 260-267.
Sohmiya, M., et al., "Effect of Long-term Administration of Recombinant Human Growth Hormone (rhGH) on Plasma Erythropoietin (EPO) and Haemoglobin Levels in Anaemic Patients with Adult GH Deficiency"—Journal of Endocrinological Invest., 2000, vol. 23, pp. 31-36.
Sohmiya, M., et al., "Effect of Long-term Administration of Recombinant Human Growth Hormone (rhGH) on Plasma Erythropoietin (EPO) and Haemoglobin Levels in Anaemic Patients with Adult GH Deficiency"—Clinical Endocrinology, 2001, vol. 55, pp. 749-754.

* cited by examiner

*Primary Examiner*—Anne-Marie Falk
*Assistant Examiner*—Magdalene K Sgagias
(74) *Attorney, Agent, or Firm*—Judy Jarecki-Black; Merial Limited; Thomas Kowalski

(57) ABSTRACT

The present invention relates to a canine pre-proGHRH polypeptide, a canine mature GHRH peptide, an isolated polynucleotide which encodes the canine pre-proGHRH or the canine mature GHRH. The invention also encompasses vectors encoding and expressing the canine pre-proGHRH or the canine GHRH which can be used to treat disease and growth hormone deficiencies by gene therapy in vertebrates, in particular in dogs.

20 Claims, 18 Drawing Sheets

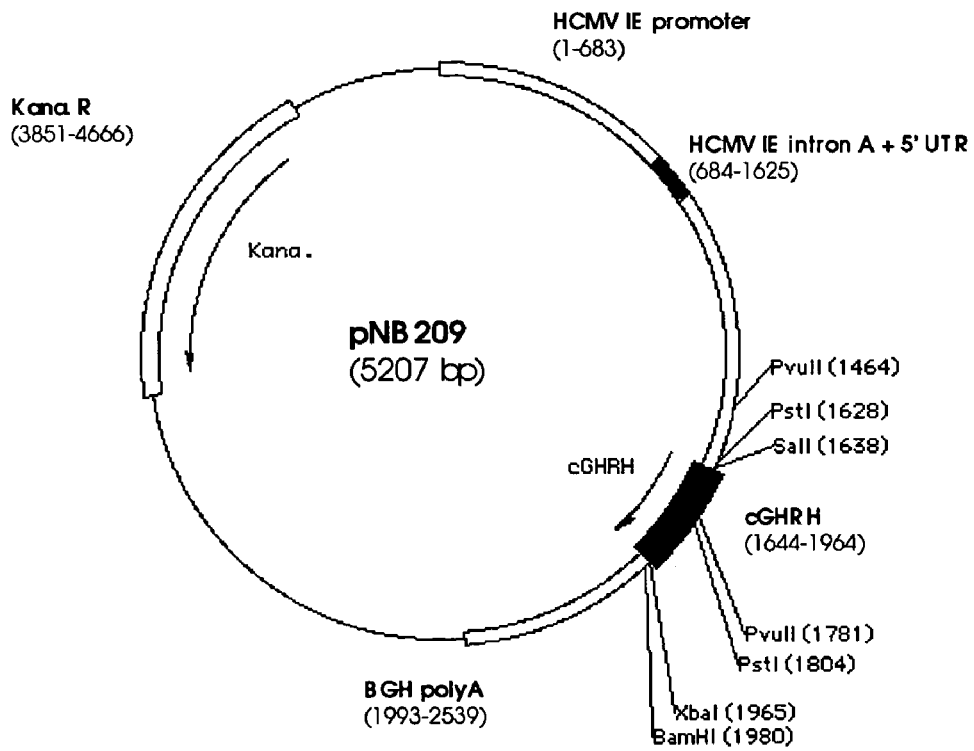

```
  1 ATG CTC CTC TGG GTG TTC TTC CTG GTG ATC CTC ACC CTC AGC AGT GGC TCC CAC TCT TCC
  1▶ M   L   L   W   V   F   F   L   V   I   L   T   L   S   S   G   S   H   S   S

61 CCG CCA TCC CTG CCC ATC AGA ATC CCT CGG TAT GCA GAC GCC ATC TTC ACC AAC AGC TAC
 21▶ P   P   S   L   P   I   R   I   P   R   Y   A   D   A   I   F   T   N   S   Y

121 CGG AAG GTG CTG GGC CAG CTG TCC GCC CGC AAG CTC CTG CAG GAC ATC ATG AGC CGG CAG
 41▶ R   K   V   L   G   Q   L   S   A   R   K   L   L   Q   D   I   M   S   R   Q

181 CAG GGA GAG AGA AAC CGG GAG CAA GGA GCA AAG GTA CGA CTC GGC CGT CAG GTG GAC AGT
 61▶ Q   G   E   R   N   R   E   Q   G   A   K   V   R   L   G   R   Q   V   D   S

241 CTG TGG GCA AGC CAA AAG CAG ATG GCA TTG GAG AAC ATC CTG GCA TCC CTG TTA CAG AAA
 81▶ L   W   A   S   Q   K   Q   M   A   L   E   N   I   L   A   S   L   L   Q   K

301 CGC AGG AAC TCC CAA GGA TGA
101▶ R   R   N   S   Q   G   *
```

FIG. 2

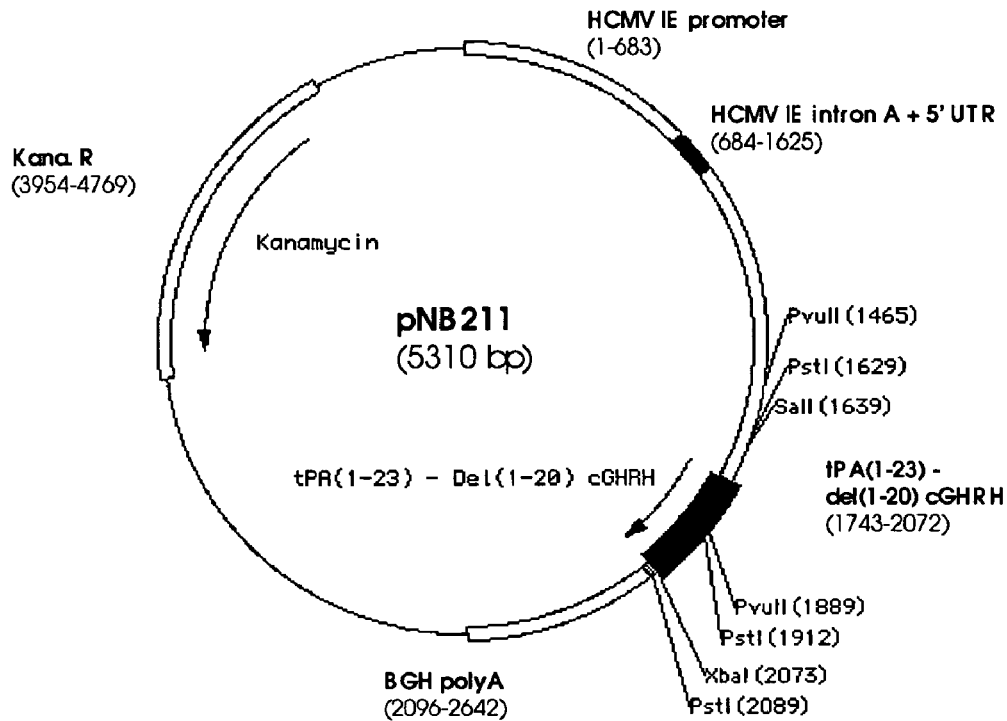

```
  1 ATG GAT GCA ATG AAG AGA GGG CTC TGC TGT GTG CTG CTG CTG TGT GGA GCA GTC TTC GTT
  1▶ M   D   A   M   K   R   G   L   C   C   V   L   L   L   C   G   A   V   F   V

61 TCG CCC AGC CCT CCA TCC CTG CCC ATC AGA ATC CCT CGG TAT GCA GAC GCC ATC TTC ACC
 21▶ S   P   S   P   P   S   L   P   I   R   I   P   R   Y   A   D   A   I   F   T

121 AAC AGC TAC CGG AAG GTG CTG GGC CAG CTG TCC GCC CGC AAG CTC CTG CAG GAC ATC ATG
 41▶ N   S   Y   R   K   V   L   G   Q   L   S   A   R   K   L   L   Q   D   I   M

181 AGC CGG CAG CAG GGA GAG AGA AAC CGG GAG CAA GGA GCA AAG GTA CGA CTC GGC CGT CAG
 61▶ S   R   Q   Q   G   E   R   N   R   E   Q   G   A   K   V   R   L   G   R   Q

241 GTG GAC AGT CTG TGG GCA AGC CAA AAG CAG ATG GCA TTG GAG AAC ATC CTG GCA TCC CTG
 81▶ V   D   S   L   W   A   S   Q   K   Q   M   A   L   E   N   I   L   A   S   L

301 TTA CAG AAA CGC AGG AAC TCC CAA GGA TGA
101▶ L   Q   K   R   R   N   S   Q   G   *
```

FIG. 4

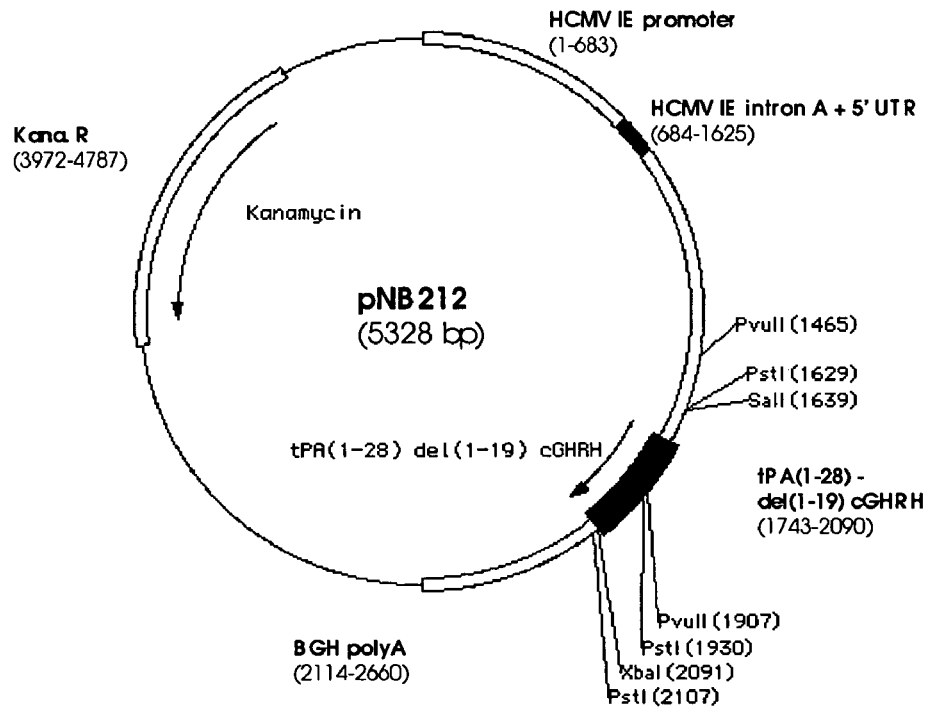

```
  1 ATG GAT GCA ATG AAG AGA GGG CTC TGC TGT GTG CTG CTG CTG TGT GGA GCA GTC TTC GTT
  1▶ M   D   A   M   K   R   G   L   C   C   V   L   L   L   C   G   A   V   F   V

61 TCG CCC AGC CAG GAA ATC CAT GCC TCC CCA CCA TCC CTG CCC ATC AGA ATC CCT CGG TAT
 21▶ S   P   S   Q   E   I   H   A   S   P   P   S   L   P   I   R   I   P   R   Y

121 GCA GAC GCC ATC TTC ACC AAC AGC TAC CGG AAG GTG CTG GGC CAG CTG TCC GCC CGC AAG
 41▶ A   D   A   I   F   T   N   S   Y   R   K   V   L   G   Q   L   S   A   R   K

181 CTC CTG CAG GAC ATC ATG AGC CGG CAG CAG GGA GAG AGA AAC CGG GAG CAA GGA GCA AAG
 61▶ L   L   Q   D   I   M   S   R   Q   Q   G   E   R   N   R   E   Q   G   A   K

241 GTA CGA CTC GGC CGT CAG GTG GAC AGT CTG TGG GCA AGC CAA AAG CAG ATG GCA TTG GAG
 81▶ V   R   L   G   R   Q   V   D   S   L   W   A   S   Q   K   Q   M   A   L   E

301 AAC ATC CTG GCA TCC CTG TTA CAG AAA CGC AGG AAC TCC CAA GGA TGA
101▶ N   I   L   A   S   L   L   Q   K   R   R   N   S   Q   G   .
```

FIG. 5

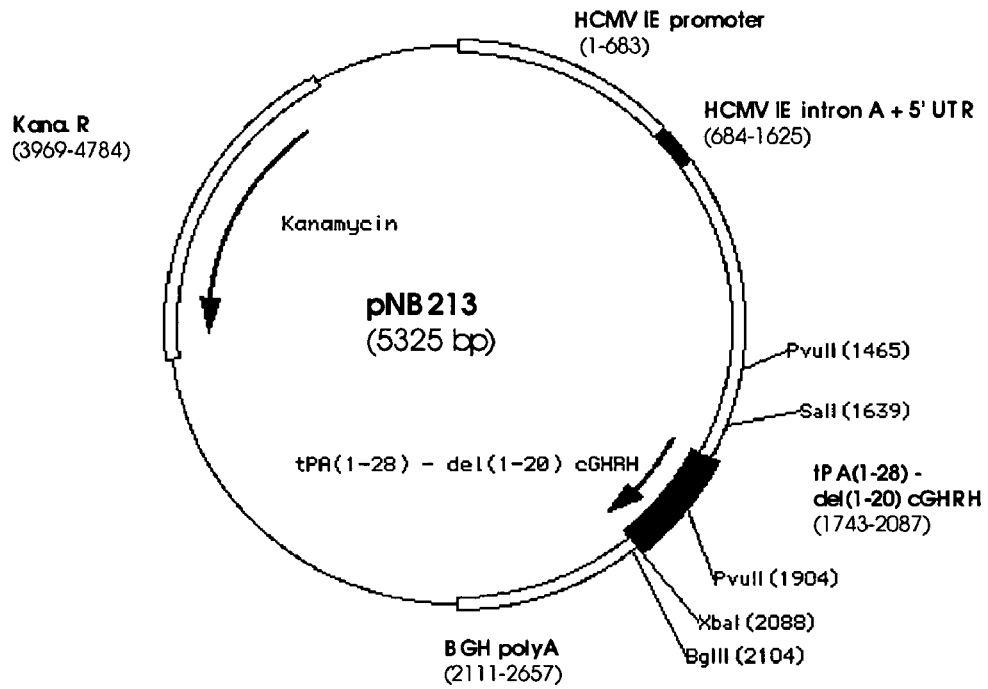

```
  1 ATG GAT GCA ATG AAG AGA GGG CTC TGC TGT GTG CTG CTG CTG TGT GGA GCA GTC TTC GTT
  1▶ M   D   A   M   K   R   G   L   C   C   V   L   L   L   C   G   A   V   F   V

61 TCG CCC AGC CAG GAA ATC CAT GCC CCT CCA TCC CTG CCC ATC AGA ATC CCT CGG TAT GCA
 21▶ S   P   S   Q   E   I   H   A   P   P   S   L   P   I   R   I   P   R   Y   A

121 GAC GCC ATC TTC ACC AAC AGC TAC CGG AAG GTG CTG GGC CAG CTG TCC GCC CGC AAG CTC
 41▶ D   A   I   F   T   N   S   Y   R   K   V   L   G   Q   L   S   A   R   K   L

181 CTG CAG GAC ATC ATG AGC CGG CAG CAG GGA GAG AGA AAC CGG GAG CAA GGA GCA AAG GTA
 61▶ L   Q   D   I   M   S   R   Q   Q   G   E   R   N   R   E   Q   G   A   K   V

241 CGA CTC GGC CGT CAG GTG GAC AGT CTG TGG GCA AGC CAA AAG CAG ATG GCA TTG GAG AAC
 81▶ R   L   G   R   Q   V   D   S   L   W   A   S   Q   K   Q   M   A   L   E   N

301 ATC CTG GCA TCC CTG TTA CAG AAA CGC AGG AAC TCC CAA GGA TGA
101▶ I   L   A   S   L   L   Q   K   R   R   N   S   Q   G   *
```

FIG. 6

```
  1 ATG GAT GCA ATG AAG AGA GGG CTC TGC TGT GTG CTG CTG CTG TGT GGA GCA GTC TTC GTT
  1▶  M   D   A   M   K   R   G   L   C   C   V   L   L   L   C   G   A   V   F   V

61 TCG CCC AGC TAC GCA GAC GCC ATC TTC ACC AAC AGC TAC CGG AAG GTG CTG GGC CAG CTG
 21▶  S   P   S   Y   A   D   A   I   F   T   N   S   Y   R   K   V   L   G   Q   L

121 TCC GCC CGC AAG CTC CTG CAG GAC ATC ATG AGC CGG CAG CAG GGA GAG AGA AAC CGG GAG
 41▶  S   A   R   K   L   L   Q   D   I   M   S   R   Q   Q   G   E   R   N   R   E

181 CAA GGA GCA AAG GTA CGA CTC TGA
 61▶  Q   G   A   K   V   R   L   *
```

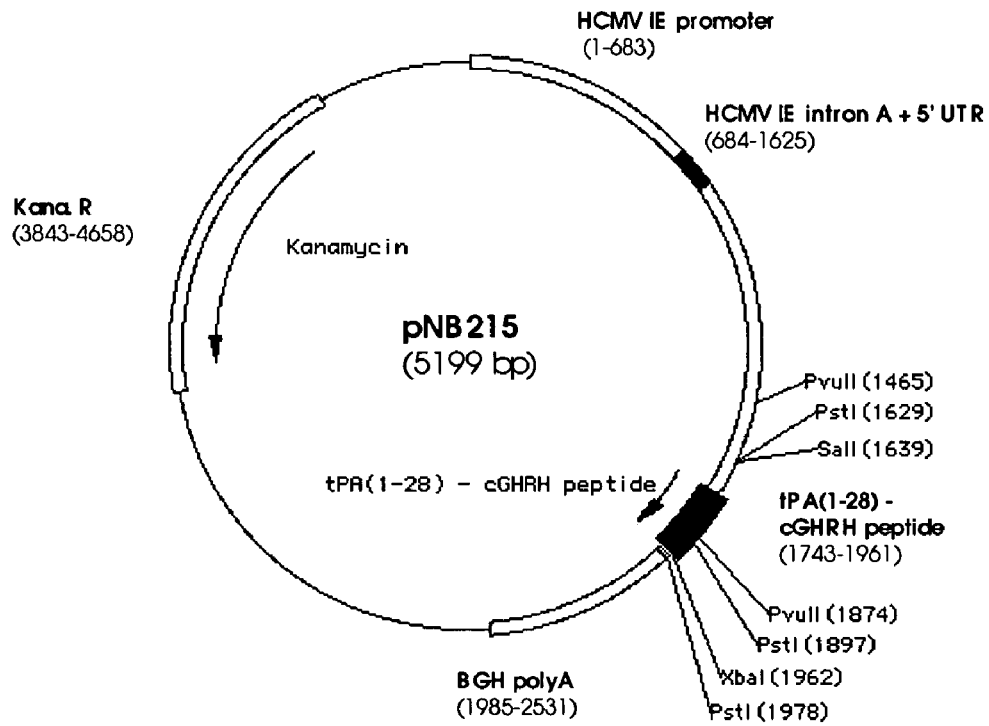

```
1   ATG GAT GCA ATG AAG AGA GGG CTC TGC TGT GTG CTG CTG CTG TGT GGA GCA GTC TTC GTT
1▶  M   D   A   M   K   R   G   L   C   C   V   L   L   L   C   G   A   V   F   V

61  TCG CCC AGC CAG GAA ATC CAT GCC TAC GCA GAC GCC ATC TTC ACC AAC AGC TAC CGG AAG
21▶ S   P   S   Q   E   I   H   A   Y   A   D   A   I   F   T   N   S   Y   R   K

121 GTG CTG GGC CAG CTG TCC GCC CGC AAG CTC CTG CAG GAC ATC ATG AGC CGG CAG CAG GGA
41▶ V   L   G   Q   L   S   A   R   K   L   L   Q   D   I   M   S   R   Q   Q   G

181 GAG AGA AAC CGG GAG CAA GGA GCA AAG GTA CGA CTC TGA
61▶ E   R   N   R   E   Q   G   A   K   V   R   L   *
```

FIG. 8

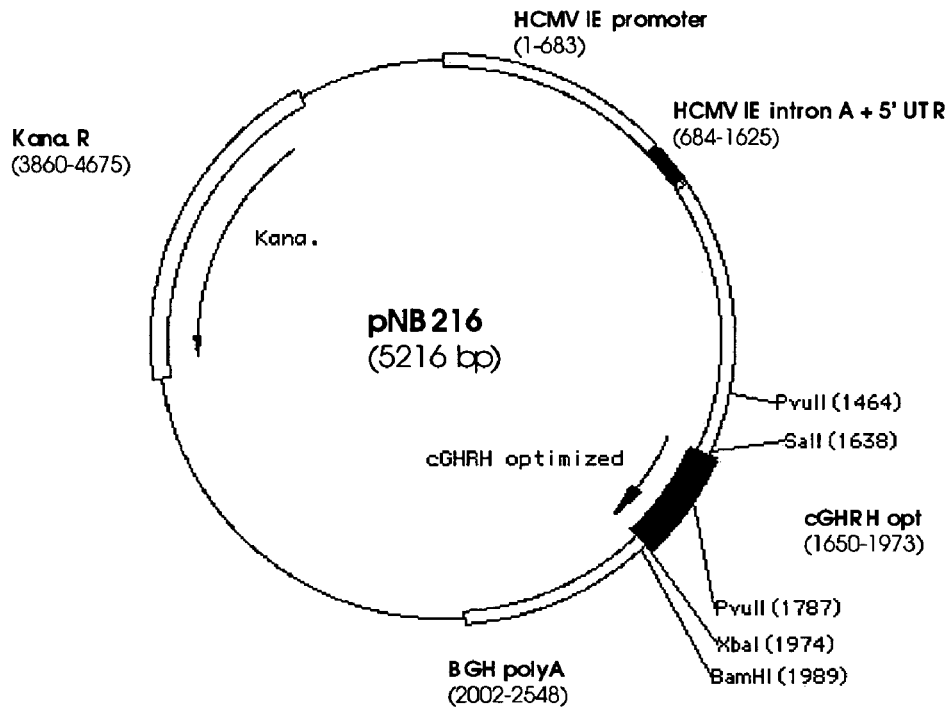

```
  1 ATG CTG CTG TGG GTG TTC TTC CTG GTG ATC CTG ACC CTG AGC AGC GGC AGC CAC AGC AGC
  1▸ M   L   L   W   V   F   F   L   V   I   L   T   L   S   S   G   S   H   S   S

61 CCC CCC AGC CTG CCC ATC CGC ATC CCC CGG TAC GCC GAC GCC ATC TTC ACC AAC AGC TAC
 21▸ P   P   S   L   P   I   R   I   P   R   Y   A   D   A   I   F   T   N   S   Y

121 CGG AAA GTG CTG GGC CAG CTG AGC GCC CGG AAG CTG CTG CAG GAC ATC ATG AGC CGC CAG
 41▸ R   K   V   L   G   Q   L   S   A   R   K   L   L   Q   D   I   M   S   R   Q

181 CAG GGC GAG CGC AAC CGC GAG CAG GGC GCC AAA GTG CGG CTG GGC CGC CAA GTG GAC AGC
 61▸ Q   G   E   R   N   R   E   Q   G   A   K   V   R   L   G   R   Q   V   D   S

241 CTG TGG GCC AGC CAG AAA CAG ATG GCC CTG GAG AAC ATC CTG GCC AGC CTG CTG CAG AAG
 81▸ L   W   A   S   Q   K   Q   M   A   L   E   N   I   L   A   S   L   L   Q   K

301 CGG CGG AAC AGC CAG GGC TGA TAA
101▸ R   R   N   S   Q   G   *   *
```

FIG. 9

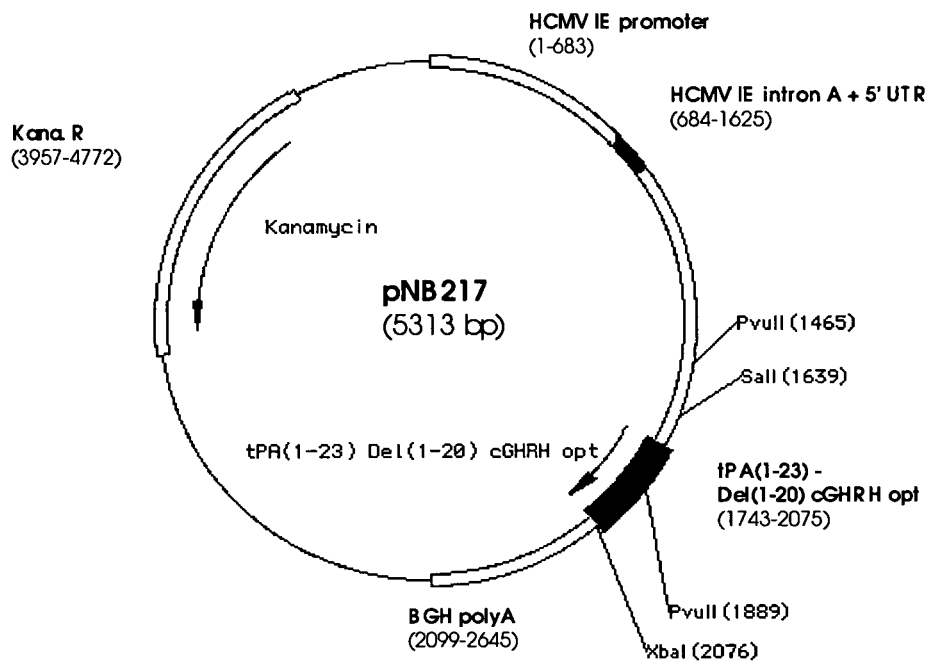

```
  1  ATG GAT GCA ATG AAG AGA GGG CTC TGC TGT GTG CTG CTG CTG TGT GGA GCA GTC TTC GTT
  1▶  M   D   A   M   K   R   G   L   C   C   V   L   L   L   C   G   A   V   F   V
 61  TCG CCC AGC CCC CCC AGC CTG CCC ATC CGC ATC CCC CGG TAC GCC GAC GCC ATC TTC ACC
 21▶  S   P   S   P   P   S   L   P   I   R   I   P   R   Y   A   D   A   I   F   T
121  AAC AGC TAC CGG AAA GTG CTG GGC CAG CTG AGC GCC CGG AAG CTG CTG CAG GAC ATC ATG
 41▶  N   S   Y   R   K   V   L   G   Q   L   S   A   R   K   L   L   Q   D   I   M
181  AGC CGC CAG CAG GGC GAG CGC AAC CGC GAG CAG GGC GCC AAA GTG CGG CTG GGC CGC CAA
 61▶  S   R   Q   Q   G   E   R   N   R   E   Q   G   A   K   V   R   L   G   R   Q
241  GTG GAC AGC CTG TGG GCC AGC CAG AAA CAG ATG GCC CTG GAG AAC ATC CTG GCC AGC CTG
 81▶  V   D   S   L   W   A   S   Q   K   Q   M   A   L   E   N   I   L   A   S   L
301  CTG CAG AAG CGG CGG AAC AGC CAG GGC TGA TAA
101▶  L   Q   K   R   R   N   S   Q   G   *   *
```

FIG. 10

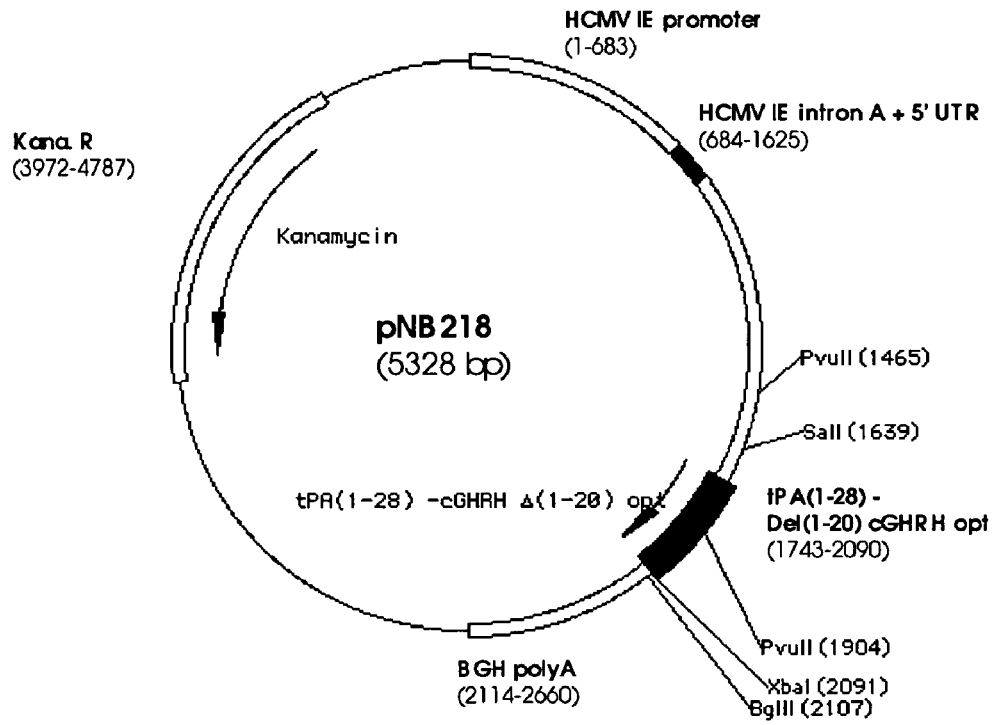

```
  1 ATG GAT GCA ATG AAG AGA GGG CTC TGC TGT GTG CTG CTG TGT GGA GCA GTC TTC GTT
 1▶ M   D   A   M   K   R   G   L   C   C   V   L   L   C   G   A   V   F   V

61 TCG CCC AGC CAG GAA ATC CAT GCC CCC CCC AGC CTG CCC ATC CGC ATC CCC CGG TAC GCC
21▶ S   P   S   Q   E   I   H   A   P   P   S   L   P   I   R   I   P   R   Y   A

121 GAC GCC ATC TTC ACC AAC AGC TAC CGG AAA GTG CTG GGC CAG CTG AGC GCC CGG AAG CTG
41▶ D   A   I   F   T   N   S   Y   R   K   V   L   G   Q   L   S   A   R   K   L

181 CTG CAG GAC ATC ATG AGC CGC CAG CAG GGC GAG CGC AAC CGC GAG CAG GGC GCC AAA GTG
61▶ L   Q   D   I   M   S   R   Q   Q   G   E   R   N   R   E   Q   G   A   K   V

241 CGG CTG GGC CGC CAA GTG GAC AGC CTG TGG GCC AGC CAG AAA CAG ATG GCC CTG GAG AAC
81▶ R   L   G   R   Q   V   D   S   L   W   A   S   Q   K   Q   M   A   L   E   N

301 ATC CTG GCC AGC CTG CTG CAG AAG CGG CGG AAC AGC CAG GGC TGA TAA
101▶ I   L   A   S   L   L   Q   K   R   R   N   S   Q   G   *   *
```

FIG. 11

```
  1  ATG GAT GCA ATG AAG AGA GGG CTC TGC TGT GTG CTG CTG CTG TGT GGA GCA GTC TTC GTT
  1▶  M   D   A   M   K   R   G   L   C   C   V   L   L   L   C   G   A   V   F   V

61  TCG CCC AGC TAC GCC GAC GCC ATC TTC ACC AAC AGC TAC CGG AAA GTG CTG GGC CAG CTG
 21▶  S   P   S   Y   A   D   A   I   F   T   N   S   Y   R   K   V   L   G   Q   L

121  AGC GCC CGG AAG CTG CTG CAG GAC ATC ATG AGC CGC CAG CAG GGC GAG CGC AAC CGC GAG
 41▶  S   A   R   K   L   L   Q   D   I   M   S   R   Q   Q   G   E   R   N   R   E

181  CAG GGC GCC AAA GTG CGG CTG TGA
 61▶  Q   G   A   K   V   R   L   *
```

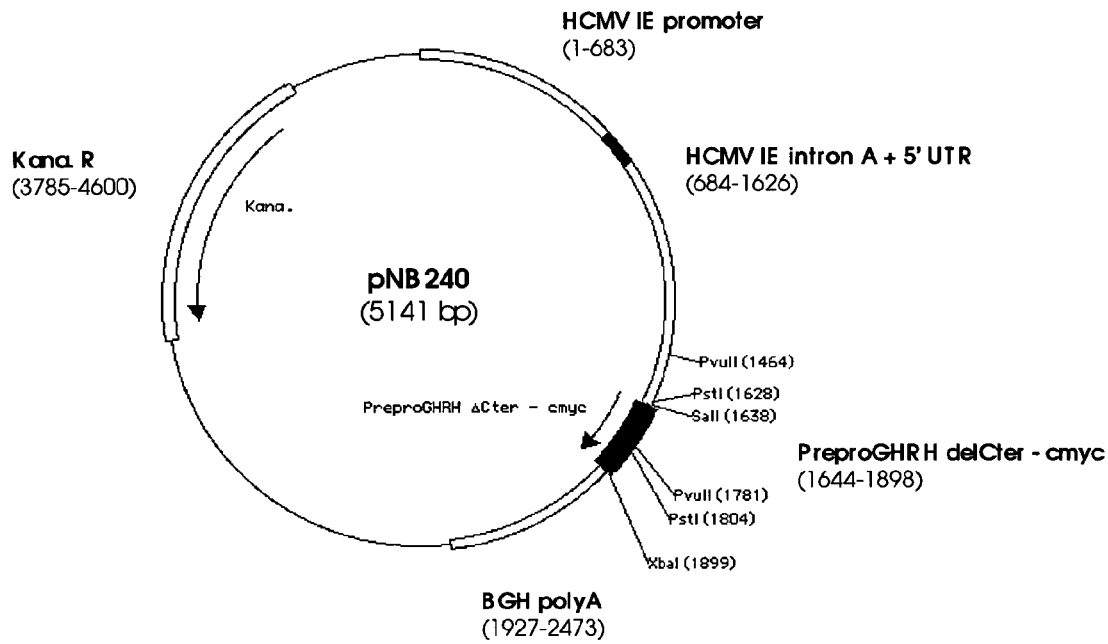

```
  1 ATG CTG CTC TGG GTG TTC TTC CTG GTG ATC CTC ACC CTC AGC AGT GGC TCC CAC TCT TCC
  1▶ M   L   L   W   V   F   F   L   V   I   L   T   L   S   S   G   S   H   S   S

61 CCA CCA TCC CTG CCC ATC AGA ATC CCT CGG TAT GCA GAC GCC ATC TTC ACC AAC AGC TAC
 21▶ P   P   S   L   P   I   R   I   P   R   Y   A   D   A   I   F   T   N   S   Y

121 CGG AAG GTG CTG GGC CAG CTG TCC GCC CGC AAG CTC CTG CAG GAC ATC ATG AGC CGG CAG
 41▶ R   K   V   L   G   Q   L   S   A   R   K   L   L   Q   D   I   M   S   R   Q

181 CAG GGA GAG AGA AAC CGG GAG CAA GGA GCA AAG GTA CGA CTC GAA CAA AAG CTT ATC TCA
 61▶ Q   G   E   R   N   R   E   Q   G   A   K   V   R   L   E   Q   K   L   I   S

241 GAA GAG GAT CTC TAA
 81▶ E   E   D   L   •
```

FIG. 14

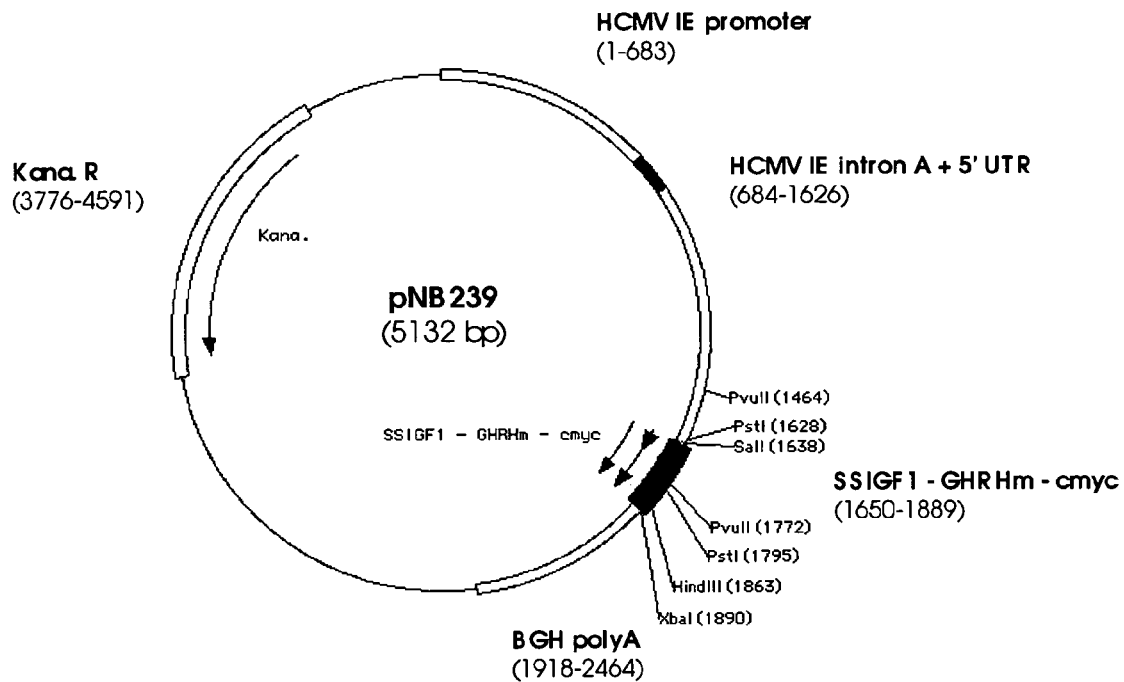

```
  1 ATG CAC ATC ATG AGC AGC AGC CAC CTG TTC TAC CTG GCC CTG TGC CTG CTG ACC TTC ACC
  1▶ M   H   I   M   S   S   S   H   L   F   Y   L   A   L   C   L   L   T   F   T

61 AGC AGC GCC ACC GCC TAC GCA GAC GCC ATC TTC ACC AAC AGC TAC CGG AAG GTG CTG GGC
 21▶ S   S   A   T   A   Y   A   D   A   I   F   T   N   S   Y   R   K   V   L   G

121 CAG CTG TCC GCC CGC AAG CTC CTG CAG GAC ATC ATG AGC CGG CAG CAG GGA GAG AGA AAC
 41▶ Q   L   S   A   R   K   L   L   Q   D   I   M   S   R   Q   Q   G   E   R   N

181 CGG GAG CAA GGA GCA AAG GTA CGA CTC GAA CAA AAG CTT ATC TCA GAA GAG GAT CTC TAA
 61▶ R   E   Q   G   A   K   V   R   L   E   Q   K   L   I   S   E   E   D   L   •
```

FIG. 15

```
  1 ATG CAC ATC ATG AGC AGC AGC CAC CTG TTC TAC CTG GCC CTG TGC CTG CTG ACC TTC ACC
  1▶ M   H   I   M   S   S   S   H   L   F   Y   L   A   L   C   L   L   T   F   T

61 AGC AGC GCC ACC GCC TAC GCA GAC GCC ATC TTC ACC AAC AGC TAC CGG AAG GTG CTG GGC
 21▶ S   S   A   T   A   Y   A   D   A   I   F   T   N   S   Y   R   K   V   L   G

121 CAG CTG TCC GCC CGC AAG CTC CTG CAG GAC ATC ATG AGC CGG CAG CAG GGA GAG AGA AAC
 41▶ Q   L   S   A   R   K   L   L   Q   D   I   M   S   R   Q   Q   G   E   R   N

181 CGG GAG CAA GGA GCA AAG GTA CGA CTC TGA
 61▶ R   E   Q   G   A   K   V   R   L   *
```

US 7,468,273 B2

CANINE GHRH GENE, POLYPEPTIDES AND METHODS OF USE

INCORPORATION BY REFERENCE

This application is a continuation in part of U.S. application Ser. No. 10/838,122 entitled: "CANINE GHRH GENE, POLYPEPTIDES AND METHODS OF USE", filed May 3, 2004 which claims priority to U.S. Provisional Application Ser. No. 60/467,405 entitled: "CANINE GHRH GENE, POLYPEPTIDES AND METHODS OF USE", filed May 1, 2003. The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to a canine pre-proGHRH polypeptide, a canine mature GHRH peptide, an isolated polynucleotide which encodes the canine pre-proGHRH or the canine mature GHRH.

In an embodiment the invention relates to a vector encoding and expressing the canine pre-proGHRH or the canine GHRH. Such a vector can be used to treat disease and growth hormone deficiencies by gene therapy in vertebrates, in particular in dogs.

In another embodiment the invention relates to a method for delivering the peptide GHRH to a vertebrate, in particular to a dog, comprising injecting the vector expressing in vivo the canine pre-proGHRH or the canine GHRH to the animal host.

The invention relates also to method of treatment of anaemia, cachexia, wound healing, bone healing, osteoporosis, obesity in vertebrates, in particular in dog.

BACKGROUND OF THE INVENTION

Growth hormone-releasing hormone (GHRH) is a hypothalamic peptide that plays a critical role in controlling the synthesis and secretion of growth hormone (GH) by the anterior pituitary. Human GHRH is a C-terminal amidated peptide of 44 amino acids. In contrast the rat GHRH is a 43 amino acids long, non-amidated peptide, which is only 67% homologous to human GHRH. It is established that GHRH originates from a precursor (pre-proGHRH) that is processed to mature GHRH by removal of the signal peptide and proteolytic cleavage at C-terminal region. The amino acid sequence of the precursor comprises 107 or 108 residues depending upon differential usage of two possible splice-acceptor sites.

The gene of the human and the rat GHRH includes five small exons separated by 4 introns and spans over 10 kilobases on genomic DNA but differs by the position and the size of the introns.

The patent application EP1052286 illustrates a non-specific method to clone the canine GHRH gene from a genomic library but the description does not disclose the nucleotide sequence of the gene or provides any guidance how to remove the introns and how to assemble the exon sequences to obtain the full coding sequence.

In farm animals, GHRH is galactopoietic with no alteration in milk composition, increases the feed to milk conversion and sustains growth, mostly through increased lean body mass. By stimulation of GH secretion, the GHRH enhances the immune functions in animals. The GHRH have a great therapeutic utility in the treatment of cachexia (Bartlett et al Cancer 1994, 73, 1499-1504 and Surgery 1995, 117, 260-267) in chronic diseases such as cancer, due to growth hormone production abnormalities, in wound healing, bone healing, retardation of the aging process, osteoporosis and in anaemia (Sohmiya et al J. Endocrinol. Invest. 2000, 23, 31-36 and Clin. Endocrinl. 2001, 55, 749-754).

Studies have shown that relatively small amounts of GHRH are required to stimulate the production and the secretion of GH. However the use of a heterologous GHRH, coming from a different animal species, may lead to a less potent stimulation of the release of GH. The therapeutic administration of heterologous GHRH peptide may also induce antibody response in the host. The DNA encoding the canine GHRH was unknown until the present invention and there was a need to make available canine GHRH in sufficient quantity to treat dogs or other animal species.

Citation or identification of any document in this application is not an admission that such document is available as prior art to the present invention.

SUMMARY OF THE INVENTION

The present invention is based, in part, on Applicants' identification of novel canine pre-proGHRH and canine mature GHRH polynucleotide and polypeptide sequences.

The present invention relates to a canine pre-proGHRH polypeptide, a canine mature GHRH peptide and isolated polynucleotides which encodes the canine pre-proGHRH or the canine mature GHRH. In an advantageous embodiment, the canine pre-proGHRH polypeptide consists essentially of the amino acid residues of SEQ ID NO: 1. In another advantageous embodiment, the canine mature GHRH peptide consists essentially of the amino acid residues of SEQ ID NO: 2.

The invention also encompasses an isolated polynucleotide, or an antisense strand that is fully complementary thereto, that consists essentially of canine pre-proGHRH, having the sequence of SEQ ID NO: 3 and an isolated polynucleotide, or an antisense strand that is fully complementary thereto, that consists essentially of canine mature GHRH, having the sequence of SEQ ID NO: 4. The polynucleotides can be DNA or RNA molecules.

In one embodiment the invention relates to a vector encoding and expressing the canine pre-proGHRH or the canine GHRH. Such a vector can be used to treat disease and growth hormone deficiencies by gene therapy in vertebrates. In advantageous embodiment, the expression vector comprises a polynucleotide that encodes a canine pre-proGHRH, wherein the polynucleotide comprises the nucleotide base sequence of SEQ ID NO: 3. In another advantageous embodiment, the expression vector comprises polynucleotide that encodes a canine mature GHRH, wherein the polynucleotide comprises the nucleotide base sequence of SEQ ID NO: 4. In an advantageous embodiment, the nucleotide base sequence is operatively linked to a promoter and optionally an enhancer.

In a particularly advantageous embodiment, the invention relates to a vector encoding and expressing the canine proGHRH, the canine proGHRH deleted of the propeptide N-terminus (corresponding to 31-106 AA) or the canine GHRH wherein a peptide signal sequence is fused to the canine proGHRH, the canine proGHRH deleted of the propeptide N-terminus (corresponding to 31-106 AA) or the canine GHRH. Advantageously, the peptide signal sequence is an insulin-like growth factor (IGF) peptide signal sequence. In a particularly advantageous embodiment, the peptide signal sequence is an IGF-1 peptide signal sequence, more advantageously, an equine IGF-1 peptide signal sequence. Such a vector can be used to treat disease and growth hormone deficiencies by gene therapy in vertebrates. In advantageous embodiment, the expression vector comprises a polynucleotide that encodes a canine pre-proGHRH, wherein the polynucleotide comprises the nucleotide base sequence of SEQ ID NO: 3. In another advantageous embodiment, the expression vector comprises polynucleotide that encodes a canine mature GHRH, wherein the polynucleotide comprises the nucleotide base sequence of SEQ ID NO: 4. In an advantageous embodiment, the nucleotide base sequence is operatively linked to a promoter and optionally an enhancer.

In another embodiment the invention relates to a method for delivering the peptide GHRH to a vertebrate, in particular to a dog, comprising injecting the vector expressing in vivo the canine pre-proGHRH or the canine GHRH to the animal host. In an advantageous embodiment, the animal host is a dog. In an advantageous embodiment, a formulation comprising a vector expressing canine GHRH or a canine pre-proGHRH and a pharmaceutically or veterinarily acceptable carrier or vehicle or excipient that facilitates delivery and expression canine GHRH or a canine pre-proGHRH the in a cell or improves the stability of the vector. Advantageously, the delivery is in vivo to an animal, advantageously a vertebrate, more advantageously, a dog. In a more advantageous embodiment, the vector in the formulation comprises the canine pre-proGHRH sequence consisting essentially of SEQ ID NO: 3 or the canine mature GHRH sequence consisting essentially of SEQ ID NO: 4.

The invention also provides for methods for delivering GHRH to an animal, advantageously a vertebrate, more advantageously a dog, comprising injecting a GHRH formulation to the animal. In an advantageous embodiment, the formulation comprises a vector expressing canine GHRH and a pharmaceutically or veterinarily acceptable carrier or vehicle or excipient.

The invention relates also to method of treatment of anaemia, cachexia, wound healing, bone healing, osteoporosis and obesity in vertebrates. The invention also relates to a method to stimulate the immune response of a vertebrate.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. As used herein, "consistently essentially of" has the meaning to explicitly exclude non-canine GHRH sequences.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 2 depicts the plasmid map and the encoded ORF of pNB209. The nucleotide sequence of the encoded ORF is SEQ ID NO: 26 and the amino acid sequence of the encoded ORF is SEQ ID NO: 27.

FIG. 4 depicts the plasmid map and the encoded ORF of pNB211. The nucleotide sequence of the encoded ORF is SEQ ID NO: 30 and the amino acid sequence of the encoded ORF is SEQ ID NO: 31.

FIG. 5 depicts the plasmid map and the encoded ORF of pNB212. The nucleotide sequence of the encoded ORF is SEQ ID NO: 32 and the amino acid sequence of the encoded ORF is SEQ ID NO: 33.

FIG. 6 depicts the plasmid map and the encoded ORF of pNB213. The nucleotide sequence of the encoded ORF is SEQ ID NO: 34 and the amino acid sequence of the encoded ORF is SEQ ID NO: 35.

FIG. 8 depicts the plasmid map and the encoded ORF of pNB215. The nucleotide sequence of the encoded ORF is SEQ ID NO: 38 and the amino acid sequence of the encoded ORF is SEQ ID NO: 39.

FIG. 9 depicts the plasmid map and the encoded ORF of pNB216. The nucleotide sequence of the encoded ORF is SEQ ID NO: 40 and the amino acid sequence of the encoded ORF is SEQ ID NO: 27.

FIG. 10 depicts the plasmid map and the encoded ORF of pNB217. The nucleotide sequence of the encoded ORF is SEQ ID NO: 41 and the amino acid sequence of the encoded ORF is SEQ ID NO: 31.

FIG. 11 depicts the plasmid map and the encoded ORF of pNB218. The nucleotide sequence of the encoded ORF is SEQ ID NO: 42 and the amino acid sequence of the encoded ORF is SEQ ID NO: 35.

FIG. 13 depicts the plasmid map and the encoded ORF of pNB220.

FIG. 14 depicts the plasmid map and the encoded ORF of pNB240. The nucleotide sequence of the encoded ORF is SEQ ID NO: 55 and the amino acid sequence of the encoded ORF is SEQ ID NO: 56.

FIG. 15 depicts the plasmid map and the encoded ORF of pNB239. The nucleotide sequence of the encoded ORF is SEQ ID NO: 57 and the amino acid sequence of the encoded ORF is SEQ ID NO: 58.

DETAILED DESCRIPTION

Figure 1:
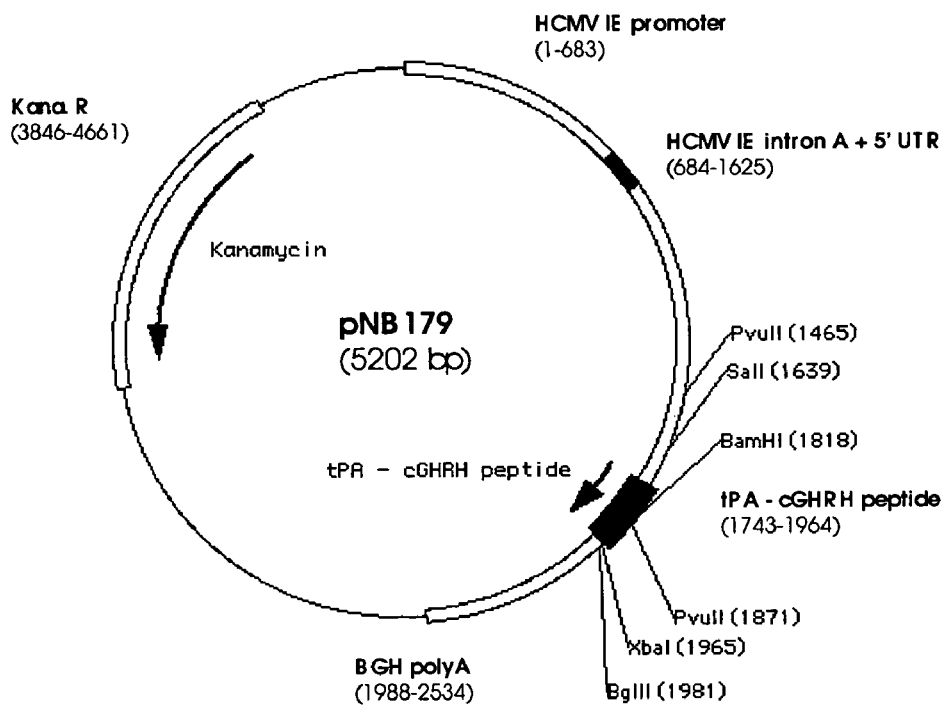
FIG. 1 depicts the plasmid map and the encoded ORF of pNB179. The nucleotide sequence of the encoded ORF is SEQ ID NO: 49 and the amino acid sequence of the encoded ORF is SEQ ID NO: 50.

The present invention is based, in part, on Applicants' identification of novel canine pre-proGHRH and canine mature GHRH polynucleotide and polypeptide sequences. Prior to the present invention, there were available GHRH peptides and coding sequences from different animal species such as mouse, rat, pig and bovine. Using a heterogous GHRH in dog may lead to to a less potent stimulation of the GH release and may induce antibody response in the host after repeated injections. The DNA encoding the canine GHRH was unknown until the present invention and there was a need to make available canine GHRH in sufficient quantity to treat dogs.

The present invention relates to a canine pre-proGHRH polypeptide having the following amino acid sequence:

H-MPLWVFFLVILTLSSGSHSSPPSLPIRIPRYADAIFTNSYRKVLGQLSARKLLQDIMSRQ (SEQ ID NO:1)
QGERNREQGAKVRLGRQVDSLWASQKQMALENILASLLQKRRNSQG-OH.

The peptide signal (prepeptide) sequence spans from Met (1) to Ser(20). The cleavage of the signal peptide can also occur after the Ser(19). The number between brackets means the amino acid position in the pre-proGHRH sequence. The H-M and G-OH means the Met amino acid at the N terminus and the Gly amino acid at the carboxy terminus of the pre-propeptide are not modified. After cleavage of the preGHRH peptide, the proGHRH peptide is cleaved after the Arg(30) and after the Leu(74) to lead to the mature GHRH peptide.

A variant of the canine pre-proGHRH polypeptide has a substitution of the amino acid Pro in position 2 by the amino acid Leu.

The present invention relates also to a canine mature GHRH peptide having the following amino acid sequence:

$R_1$-YADAIFTNSYRKVLGQLSARKLLQDIMSRQQGERNREQGAKVRL-$R_2$    (SEQ ID NO:2)

wherein $R_1$ is hydrogen or H-Met and $R_2$ is OH or $NH_2$. The H-Met or the H—Y at the N terminus means that the methionine or the tyrosine are not modified. The L-OH or L-NH2 at the carboxy terminus of the mature peptide means that the leucine amino acid is either unmodified or amidated.

In another embodiment the invention comprises a canine mature GHRH analogue with improved stability. This analogue has at least one amino acid substitution selected among the group consisting of Tyr(1) to His(1), Ala(2) to Val(2), Gly(15) to Ala(15), Met(27) to Leu(27) or Ser(28) to Asn(28). The number between parentheses means the amino acid position in the mature GHRH sequence. These amino acid substitutions can be introduced in the canine pre-proGHRH polypeptide. It is routine experimentation for one of skill in the art to make such directed amino acid substitutions. For example, but not by limitation, site-directed mutagenesis of the canine mature GHRH polynucleotide can be carried out to obtain a mutant canine mature GHRH peptide with one or more of the above-listed amino acid substitutions. The gene can also be synthetized chemically using methods known in the art.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The present invention encompasses an isolated polynucleotide encoding the canine pre-proGHRH having the sequence and fragments:

```
5'-ATGCCACTCTGGGTGTTCTTCCTGGTGATCCTCACCCTCAGCAGTGGCTCCCACTC  (SEQ ID NO:3)
TTCCCCGCCATCCCTGCCCATCAGAATCCCTCGGTATGCAGACGCCATCTTCACC
AACAGCTACCGGAAGGTGCTGGGCCAGCTGTCCGCCCGCAAGCTCCTGCAGGAC
ATCATGAGCCGGCAGCAGGGAGAGAGAAACCGGGAGCAAGGAGCAAAGGTACG
ACTCGGCCGTCAGGTGGACAGTCTGTGGGCAAGCCAAAAGCAGATGGCATTGGA
GAACATCCTGGCATCCCTGTTACAGAAACGCAGGAACTCCCAAGGATGA-3'.
```

The invention also provides for a variant of the polynucleotide encoding the canine pre-proGHRH has a substitution of the nucleotides C and A in position 5 and 6 by T and G, respectively.

The present invention also comprises an isolated polynucleotide encoding the canine mature GHRH having the sequence:

```
5'-TATGCAGACGCCATCTTCACCAACAGCTACCGGAAGGTGCTGGGCCAGCTGTCCG  (SEQ ID NO:4)
CCCGCAAGCTCCTGCAGGACATCATGAGCCGGCAGCAGGGAGAGAGAAACCGG
GAGCAAGGAGCAAAGGTACGACTC-3'.
```

A "polynucleotide" is a polymeric form of nucleotides of any length, which contain deoxyribonucleotides, ribonucleotides, and analogs in any combination. Polynucleotides may have three-dimensional structure, and may perform any function, known or unknown. The term "polynucleotide" includes double-, single-stranded, and triple-helical molecules. Unless otherwise specified or required, any embodiment of the invention described herein that is a polynucleotide encompasses both the double stranded form and each of two complementary forms known or predicted to make up the double stranded form of either the DNA, RNA or hybrid molecule.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially free of the materials with which it is associated in its native environment. By substantially free, is meant at least 50%, advantageously at least 70%, more advantageously at least 80%, and even more advantageously at least 90% free of these materials.

The invention further comprises a complementary strand to the GHRH polynucleotide.

The complementary strand can be polymeric and of any length, and can contain deoxyribonucleotides, ribonucleotides, and analogs in any combination.

Hybridization reactions can be performed under conditions of different "stringency." Conditions that increase stringency of a hybridization reaction are well known. See for example, "Molecular Cloning: A Laboratory Manual", second edition (Sambrook et al. 1989). Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2 or more washing steps; wash incubation times of 1, 2, or 15 minutes; and wash solutions of 6×SSC, 1×SSC, 0.1×SSC, or deionized water.

The invention further encompasses polynucleotides encoding functionally equivalent variants and derivatives of the canine GHRH polypeptides and functionally equivalent fragments thereof which may enhance, decrease or not significantly affect properties of the polypeptides encoded thereby. These functionally equivalent variants, derivatives, and fragments display the ability to retain canine GHRH activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan.

In another embodiment the invention comprises a canine pre-proGHRH polypeptide variant having at least at least 87%, at least 88%, at least 89%, at least 90%, at least 91%, at least 92%, at least 93%, at least 94%, at least 95%, at least 96%, at least 97%, at least 98% or at least 99% homology or identity to SEQ ID NO: 1.

In another embodiment the invention comprises a canine mature GHRH polypeptide variant having at least 97%, at least 97.5%, at least 98%, at least 98.5%, or at least 99% homology or identity to SEQ ID NO: 2.

In another embodiment the invention comprises a variant of the polynucleotide encoding the canine pre-proGHRH having at least 86.5%, at least 87%, at least 87.5%, at least 88%, at least 88.5%, at least 89%, at least 89.5%, at least 90%, at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98% at least 98.5%, at least 99% or at least 99.5% homology or identity to SEQ ID NO: 3. The invention encompasses also a polynucleotide encoding a canine pre-proGHRH analogue. In an advantageous embodiment, the canine pre-proGHRH analogue has at least 86.5%, at least 87%, at least 87.5%, at least 88%, at least 88.5%, at least 89%, at least 89.5%, at least 90%, at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98% at least 98.5%, or at least 99% or at least 99.5% homology or identity to SEQ ID NO: 1.

In another embodiment the invention comprises a variant of the polynucleotide encoding the canine mature GHRH having 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98% at least 98.5%, at least 99% or at least 99.5% homology or identity to SEQ ID NO: 4. The invention encompasses also a polynucleotide encoding a canine mature GHRH analogue. In an advantageous embodiment, the canine mature GHRH analogue has 97.5%, at least 98% at least 98.5%, at least 99% or at least 99.5% homology or identity to SEQ ID NO: 2.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

In general, comparison of amino acid sequences is accomplished by aligning an amino acid sequence of a polypeptide of a known structure with the amino acid sequence of a the polypeptide of unknown structure. Amino acids in the sequences are then compared and groups of amino acids that are homologous are grouped together. This method detects conserved regions of the polypeptides and accounts for amino acid insertions and deletions. Homology between amino acid sequences can be determined by using commercially available algorithms (see also the description of homology above). In addition to those otherwise mentioned herein, mention is made too of the programs BLAST, gapped BLAST, BLASTN, BLASTP, and PSI-BLAST, provided by the National Center for Biotechnology Information. These programs are widely used in the art for this purpose and can align homologous regions of two amino acid sequences.

In all search programs in the suite the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Alternatively or additionally, the term "homology" or "identity", for instance, with respect to a nucleotide or amino acid sequence, can indicate a quantitative measure of homology between two sequences. The percent sequence homology can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}=8$; $N_{dif}=2$).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur & Lipman, Proc Natl Acad Sci USA 1983; 80: 726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

And, without undue experimentation, the skilled artisan can consult with many other programs or references for determining percent homology.

The invention further encompasses the canine GHRH polynucleotides contained in a vector molecule or an expression vector and operably linked to a promoter element and optionally to an enhancer.

The invention further encompasses the canine GHRH polynucleotides contained in a vector molecule or an expression vector wherein a peptide signal sequence is fused to the canine proGHRH, the canine proGHRH deleted of the propeptide N-terminus (corresponding to 31-106 AA) or the canine GHRH. Advantageously, the peptide signal sequence is an insulin-like growth factor (IGF) peptide signal sequence. In a particularly advantageous embodiment, the peptide signal sequence is an IGF-1 peptide signal sequence, more advantageously, an equine IGF-1 peptide signal sequence. One of skill in the art may optimize the expression of the canine proGHRH, the canine proGHRH deleted of the propeptide N-terminus (corresponding to 31-106 AA) or the canine GHRH nucleotide sequence fused to the peptide signal sequence by removing cryptic splice sites, e.g., by adapting the codon usage by introducing a Kozak consensus sequence before the start codon to improve expression.

In an advantageous embodiment, the promoter is the promoter of the cytomegalovirus (CMV) immediate early gene. In another advantageous embodiment, the promoter and/or enhancer elements are oxygen-inducible. Examples of oxygen-inducible promoters and/or enhancers that can be used in the methods of the present invention include, but are not limited to, early growth response-1 (Egr1) promoter (see, e.g., Park et al., J Clin Invest. 2002 August; 110 (3): 403-1), hypoxia-inducible factor (HIF) inducible enhancers (see e.g., Cuevas et al., Cancer Res. 2003 October 15; 63 (20): 6877-84) and Mn-superoxide dismutase (Mn-SOD) promoters (see, e.g., Gao et al., Gene. 1996 October 17; 176 (1-2): 269-70).

In another embodiment, the enhancers and/or promoters include various cell or tissue specific promoters (e.g., muscle, erdothelial cell, liver, somatic cell or stem cell), various viral promoters and enhancers and various GHRH DNA sequences isogenically specific for each animal species. For example, if the canine GHRH is expressed in a canine muscle cell, the enhancers and/or promoters can be specific to a canine muscle cell in order to optimize expression of canine GHRH. Examples of muscle-specific promoters and enhancers have been described are are known to one of skill in the art (see, e.g., Li et al., Gene Ther. 1999 December; 6 (12): 2005-11; Li et al., Nat Biotechnol. 1999 March; 17 (3): 241-5 and Loirat et al., Virology. 1999 July 20; 260 (1): 74-83; the disclosures of which are incorporated by reference in their entireties).

Promoters and enhancers that may be employed in the present invention include, but are not limited to LTR or the Rous sarcoma virus, TK of HSV-1, early or late promoter of SV40, adenovirus major late (MLP), phosphoglycerate kinase, metallothionein, α-1 antitrypsin, albumin, collagenese, elastase I, β-actin, β-globin, γ-globin, α-fetoprotein, muscle creatin kinase.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of therapy, and may optionally be in the form of an expression cassette. As used herein, a vector need not be capable of replication in the ultimate target cell or subject. The term includes cloning vectors also included are viral vectors.

The term "recombinant" means a polynucleotide semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide, may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, polyadenylation sites, additional transcription units under control of the same or a different promoter, sequences that permit cloning, expression, homologous recombination, and transformation of a host cell, and any such construct as may be desirable to provide embodiments of this invention.

The present invention encompasses a vector expressing the canine pre-proGHRH, the canine mature GHRH, the canine proGHRH or variants or analogues or fragments. For the mature GHRH or the proGHRH, preferably the nucleotide sequence encoding the peptide is preceded immediately by a nucleotide sequence in frame encoding a peptide signal in order to get the GHRH secreted in the extra cellular medium. The signal sequence can be the natural sequence from the pre-proGHRH or a peptide signal from a secreted protein e.g. the signal peptide from the tissue plasminogen activator protein (tPA), in particular the human tPA (S. Friezner Degen et al J. Biol. Chem. 1996, 261, 6972-6985; R. Rickles et al J. Biol. Chem. 1988, 263, 1563-1569; D. Berg. et al Biochem. Biophys. Res. Commun. 1991, 179, 1289-1296), or the signal peptide from the Insulin-like growth factor 1 (IGF1), in particular the equine IGF1 (K. Otte et al. Gen. Comp. Endocrinol. 1996, 102 (1), 11-15), the canine IGF1 (P. Delafontaine et al. Gene 1993, 130, 305-306), the feline IGF1 (WO-A-03/022886), the bovine IGF1 (S. Lien et al. Mamm. Genome 2000, 11 (10), 877-882), the porcine IGF1 (M. Muller et al. Nucleic Acids Res. 1990, 18 (2), 364), the chicken IGF1 (Y. Kajimoto et al. Mol. Endocrinol. 1989, 3 (12), 1907-1913), the turkey IGF1 (GenBank accession number AF074980). The signal peptide from IGF1 may be natural or optimized, in particular optimized by removing cryptic splice sites and/or by adapting the codon usage. For the mature GHRH Gly and Arg can be added at the C-terminus of the peptide in the coding polynucleotide sequence in order to obtain amidation.

Elements for the expression of canine GHRH are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a polyprotein fragment, e.g. canine GHRH, advantageously, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

Methods for making and/or administering a vector or recombinants or plasmid for expression of gene products of genes of the invention either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450 and 6; 312,683; U.S. patent application Ser. No. 920,197, filed Oct. 16, 1986; WO 90/01543; WO91/11525; WO 94/16716; WO 96/39491; WO 98/33510; EP 265785; EP 0 370 573; Andreansky et al., Proc. Natl. Acad. Sci. USA 1996; 93: 11313-11318; Ballay et al., EMBO J. 1993; 4: 3861-65; Felgner et al., J. Biol. Chem. 1994; 269: 2550-2561; Frolov et al., Proc. Natl. Acad. Sci. USA 1996; 93: 11371-11377; Graham, Tibtech 1990; 8: 85-87; Grunhaus et al., Sem. Virol. 1992; 3: 237-52; Ju et al., Diabetologia 1998; 41: 736-739; Kitson et al., J. Virol. 1991;

65: 3068-3075; McClements et al., Proc. Natl. Acad. Sci. USA 1996; 93: 11414-11420; Moss, Proc. Natl. Acad. Sci. USA 1996; 93: 11341-11348; Paoletti, Proc. Natl. Acad. Sci. USA 1996; 93: 11349-11353; Pennock et al., Mol. Cell. Biol. 1984; 4: 399-406; Richardson (Ed), Methods in Molecular Biology 1995; 39, "Baculovirus Expression Protocols," Humana Press Inc.; Smith et al. (1983) Mol. Cell. Biol. 1983; 3: 2156-2165; Robertson et al., Proc. Natl. Acad. Sci. USA 1996; 93: 11334-11340; Robinson et al., Sem. Immunol. 1997; 9: 271; and Roizman, Proc. Natl. Acad. Sci. USA 1996; 93: 11307-11312. Thus, the vector in the invention can be any suitable recombinant virus or virus vector, such as a poxvirus (e.g., vaccinia virus, avipox virus, canarypox virus, fowlpox virus, raccoonpox virus, swinepox virus, etc.), adenovirus (e.g., human adenovirus, canine adenovirus), herpesvirus (e.g. canine herpesvirus), baculovirus, retrovirus, etc. (as in documents incorporated herein by reference); or the vector can be a plasmid. The herein cited and incorporated herein by reference documents, in addition to providing examples of vectors useful in the practice of the invention, can also provide sources for non-canine GHRH peptides or fragments thereof, e.g., non-canine mature GHRH peptides, non-canine pre-proGHRH peptides, non-canine preGHRH peptides, non-canine proGHRH peptides or fragments thereof, cytokines, etc. to be expressed by vector or vectors in, or included in, the compositions of the invention.

The present invention also relates to preparations comprising vectors, such as expression vectors, e.g., therapeutic compositions. The preparations can comprise, consist essentially of, or consist of one or more vectors, e.g., expression vectors, such as in vivo expression vectors, comprising, consisting essentially or consisting of (and advantageously expressing) one or more of the GHRH polynucleotides. Advantageously, the vector contains and expresses a polynucleotide that includes, consists essentially of, or consists of a coding region encoding canine GHRH, in a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of canine GHRH or a fragment thereof.

According to another embodiment, the vector or vectors in the preparation comprise, or consist essentially of, or consist of polynucleotide(s) encoding one or more proteins or fragment(s) thereof of canine GHRH, the vector or vectors have expression of the polynucleotide(s). The inventive preparation advantageously comprises, consists essentially of, or consists of, at least two vectors comprising, consisting essentially of, or consisting of, and advantageously also expressing, advantageously in vivo under appropriate conditions or suitable conditions or in a suitable host cell, polynucleotides from different canine GHRH isolates encoding the same proteins and/or for different proteins, but advantageously for the same proteins. Preparations containing one or more vectors containing, consisting essentially of or consisting of polynucleotides encoding, and advantageously expressing, advantageously in vivo, canine GHRH peptide, fusion protein or an epitope thereof. The invention is also directed at mixtures of vectors that contain, consist essentially of, or consist of coding for, and express, different GHRH, e.g., GHRH from different species such as, but not limited to, cats, cows, goats, humans, mice, monkeys, pigs, rats and sheep, in addition to dogs.

According to one embodiment of the invention, the expression vector is a viral vector, in particular an in vivo expression vector. In an advantageous embodiment, the expression vector is an adenovirus vector. Advantageously, the adenovirus is a human Ad5 vector, an E1-deleted and/or an E3-deleted adenovirus.

In one particular embodiment the viral vector is a poxvirus, e.g. a vaccinia virus or an attenuated vaccinia virus, (for instance, MVA, a modified Ankara strain obtained after more than 570 passages of the Ankara vaccine strain on chicken embryo fibroblasts; see Stickl & Hochstein-Mintzel, Munch. Med. Wschr., 1971, 113, 1149-1153; Sutter et al., Proc. Natl. Acad. Sci. U.S.A., 1992, 89,10847-10851; available as ATCC VR-1508; or NYVAC, see U.S. Pat. No. 5,494,807, for instance, Examples 1 to 6 and et seq of U.S. Pat. No. 5,494,807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO96/40241), an avipox virus or an attenuated avipox virus (e.g., canarypox, fowlpox, dovepox, pigeonpox, quailpox, ALVAC or TROVAC; see, e.g., U.S. Pat. Nos. 5,505,941, 5,494,807), swinepox, raccoonpox, camelpox, or myxomatosis virus.

According to another embodiment of the invention, the poxvirus vector is a canarypox virus or a fowlpox virus vector, advantageously an attenuated canarypox virus or fowlpox virus. In this regard, is made to the canarypox available from the ATCC under access number VR-111. Attenuated canarypox viruses are described in U.S. Pat. No. 5,756,103 (ALVAC) and WO01/05934. Numerous fowlpox virus vaccination strains are also available, e.g. the DIFTOSEC CT strain marketed by MERIAL and the NOBILIS VARIOLE vaccine marketed by INTERVET; and, reference is also made to U.S. Pat. No. 5,766,599 which pertains to the atenuated fowlpox strain TROVAC.

For information on the method to generate recombinants thereof and how to administer recombinants thereof, the skilled artisan can refer documents cited herein and to WO90/12882, e.g., as to vaccinia virus mention is made of U.S. Pat. Nos. 4,769,330, 4,722,848, 4,603,112, 5,110,587, 5,494,807, and 5,762,938 inter alia; as to fowipox, mention is made of U.S. Pat. Nos. 5,174,993, 5,505,941 and 5,766,599 inter alia; as to canarypox mentionis made of U.S. Pat. No. 5,756,103 inter alia; as to swinepox mention is made of U.S. Pat. No. 5,382,425 inter alia; and, as to raccoonpox, mention is made of WO00/03030 inter alia.

When the expression vector is a vaccinia virus, insertion site or sites for the polynucleotide or polynucleotides to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, advantageously the insertion site or sites are ORF(s) C3, C5 and/or C6; see also documents cited herein, especially those pertaining to canarypox virus. In the case of fowlpox, advantageously the insertion site or sites are ORFs F7 and/or F8; see also documents cited herein, especially those pertaining to fowlpox virus. The insertion site or sites for MVA virus area advantageously as in various publications, including Carroll M. W. et al., Vaccine, 1997, 15 (4), 387-394; Stittelaar K. J. et al., J. Virol., 2000, 74 (9), 4236-4243; Sutter G. et al., 1994, Vaccine, 12 (11), 1032-1040; and, in this regard it is also noted that the complete MVA genome is described in Antoine G., Virology, 1998, 244, 365-396, which enables the skilled artisan to use other insertion sites or other promoters.

Advantageously, the polynucleotide to be expressed is inserted under the control of a specific poxvirus promoter, e.g., the vaccinia promoter 7.5 kDa (Cochran et al., J. Virology, 1985, 54, 30-35), the vaccinia promoter 13L (Riviere et al., J. Virology, 1992, 66, 3424-3434), the vaccinia promoter HA (Shida, Virology, 1986, 150, 451-457), the cowpox promoter ATI (Funahashi et al., J. Gen. Virol., 1988, 69, 35-47), the vaccinia promoter H6 (Taylor J. et al., Vaccine, 1988, 6, 504-508; Guo P. et al. J. Virol., 1989, 63, 4189-4198; Perkus M. et al., J. Virol., 1989, 63, 3829-3836), inter alia.

In a particular embodiment the viral vector is an adenovirus, such as a human adenovirus (HAV) or a canine adenovirus (CAV).

In one embodiment the viral vector is a human adenovirus, in particular a serotype 5 adenovirus, rendered incompetent for replication by a deletion in the E1 region of the viral genome, in particular from about nucleotide 459 to about nucleotide 3510 by reference to the sequence of the hAd5 disclosed in Genbank under the accession number M73260 and in the referenced publication J. Chroboczek et al Virol. 1992, 186, 280-285. The deleted adenovirus is propagated in E1-expressing 293 (F. Graham et al J. Gen. Virol. 1977, 36, 59-72) or PER cells, in particular PER.C6 (F. Falloux et al Human Gene Therapy 1998, 9, 1909-1917). The human adenovirus can be deleted in the E3 region, in particular from about nucleotide 28592 to about nucleotide 30470. The deletion in the E1 region can be done in combination with a deletion in the E3 region (see, e.g. J. Shriver et al. Nature, 2002, 415, 331-335, F. Graham et al Methods in Molecular Biology Vol 0.7: Gene Transfer and Expression Protocols Edited by E. Murray, The Human Press Inc, 1991, p 109-128; Y. Ilan et al Proc. Natl. Acad. Sci. 1997, 94, 2587-2592; U.S. Pat. Nos. 6,133,028; 6,692,956; S. Tripathy et al Proc. Natl. Acad. Sci. 1994, 91, 11557-11561; B. Tapnell Adv. Drug Deliv. Rev. 1993, 12, 185-199; X. Danthinne et al Gene Thrapy 2000, 7, 1707-1714; K. Berkner Bio Techniques 1988, 6, 616-629; K. Berkner et al Nucl. Acid Res. 1983, 11, 6003-6020; C. Chavier et al J. Virol. 1996, 70, 4805-4810). The insertion sites can be the E1 and/or E3 loci (region) eventually after a partial or complete deletion of the E1 and/or E3 regions. Advantageously, when the expression vector is an adenovirus, the polynucleotide to be expressed is inserted under the control of a promoter functional in eukaryotic cells, such as a strong promoter, preferably a cytomegalovirus immediate-early gene promoter (CMV-IE promoter), in particular the enhancer/promoter region from about nucleotide −734 to about nucleotide +7 in M. Boshart et al Cell 1985, 41, 521-530 or the enhancer/promoter region from the pCI vector from Promega Corp. The CMV-IE promoter is advantageously of murine or human origin. The promoter of the elongation factor 1 a can also be used. In one particular embodiment a promoter regulated by hypoxia, e.g. the promoter HRE described in K. Boast et al Human Gene Therapy 1999, 13, 2197-2208), can be used. A muscle specific promoter can also be used (X. Li et al Nat. Biotechnol. 1999, 17, 241-245). Strong promoters are also discussed herein in relation to plasmid vectors. In one embodiment, a splicing sequence can be located downstream of the enhancer/promoter region. For example, the intron 1 isolated from the CMV-IE gene (R. Stenberg et al J. Virol. 1984, 49, 190), the intron isolated from the rabbit or human β-globin gene, in particular the intron 2 from the b-globin gene, the intron isolated from the immunoglobulin gene, a splicing sequence from the SV40 early gene or the chimeric intron sequence isolated from the pCI vector from Promege Corp. comprising the human P-globin donor sequence fused to the mouse immunoglobulin acceptor sequence (from about nucleotide 890 to about nucleotide 1022 in Genbank under the accession number CVU47120). A poly(A) sequence and terminator sequence can be inserted downstream the polynucleotide to be expressed, e.g. a bovine growth hormone gene, in particular from about nucleotide 2339 to about nucleotide 2550 in Genbank under the accession number BOVGHRH, a rabbit β-globin gene or a SV40 late gene polyadenylation signal.

In another embodiment the viral vector is a canine adenovirus, in particular a CAV-2 (see, e.g. L. Fischer et al. Vaccine, 2002, 20, 3485-3497; U.S. Pat. Nos. 5,529,780; 5,688,920; PCT Application No. WO95/14102). For CAV, the insertion sites can be in the E3 region and/or in the region located between the E4 region and the right ITR region (see U.S. Pat. Nos. 6,090,393 ; 6,156,567). In one embodiment the insert is under the control of a promoter, such as a cytomegalovirus immediate-early gene promoter (CMV-IE promoter) or a promoter already described for a human adenovirus vector. A poly(A) sequence and terminator sequence can be inserted downstream the polynucleotide to be expressed, e.g. a bovine growth hormone gene or a rabbit β-globin gene polyadenylation signal.

In another particular embodiment the viral vector is a herpesvirus such as a canine herpesvirus (CHV) or a feline herpesvirus (FHV). For CHV, the insertion sites may be in particular in the thymidine kinase gene, in the ORF3, or in the UL43 ORF (see U.S. Pat. No. 6,159,477). In one embodiment the polynucleotide to be expressed is inserted under the control of a promoter functional in eukaryotic cells, advantageously a CMV-IE promoter (murine or human). In one particular embodiment a promoter regulated by hypoxia, e.g. the promoter HRE described in K. Boast et al Human Gene Therapy 1999, 13, 2197-2208), can be used. A poly(A) sequence and terminator sequence can be inserted downstream the polynucleotide to be expressed, e.g. bovine growth hormone or a rabbit β-globin gene polyadenylation signal.

According to a yet further embodiment of the invention, the expression vector is a plasmid vector or a DNA plasmid vector, in particular an in vivo expression vector. In a specific, non-limiting example, the pVR1020 or 1012 plasmid (VICAL Inc.; Luke C. et al., Journal of Infectious Diseases, 1997, 175, 91-97; Hartikka J. et al., Human Gene Therapy, 1996, 7, 1205-1217) can be utilized as a vector for the insertion of a polynucleotide sequence. The pVR1020 plasmid is derived from pVR1012 and contains the human tPA signal sequence. In one embodiment the human tPA signal comprises from amino acid M(1) to amino acid S(23) in Genbank under the accession number HUMTPA14. In another specific, non-limiting example, the plasmid utilized as a vector for the insertion of a polynucleotide sequence can contain the signal peptide sequence of equine IGF1 from amino acid M(24) to amino acid A(48) in Genbank under the accession number U28070.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide encoding the canine GHRH mature, the canine pre-proGHRH, the canine proGHRH, the propeptide GHRH deleted of the propeptide N-terminus (corresponding to 31-106 AA), variant, analog or fragment, operably linked to a promoter or under the control of a promoter or dependent upon a promoter. In general, it is advantageous to employ a strong promoter functional in eukaryotic cells. The preferred strong promoter is the immediate early cytomegalovirus promoter (CMV-IE) of human or murine origin, or optionally having another origin such as the rat or guinea pig. The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No. WO87/03905. The CMV-IE promoter is advantageously a human CMV-IE (Boshart M. et al., Cell., 1985, 41, 521-530) or murine CMV-IE.

In more general terms, the promoter has either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa M. et al., Vaccine, 2000, 18, 2337-2344), or the actin promoter (Miyazaki J. et al., Gene, 1989, 79, 269-277).

Functional sub fragments of these promoters, i.e., portions of these promoters that maintain an adequate promoting activity, are included within the present invention, e.g. truncated CMV-IE promoters according to PCT Application No. WO98/00166 or U.S. Pat. No. 6,156,567 can be used in the practice of the invention. A promoter in the practice of the invention consequently includes derivatives and sub fragments of a full-length promoter that maintain an adequate promoting activity and hence function as a promoter, preferably promoting activity substantially similar to that of the actual or full-length promoter from which the derivative or sub fragment is derived, e.g., akin to the activity of the truncated CMV-IE promoters of U.S. Pat. No. 6,156,567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub fragments.

Preferably, the plasmids comprise or consist essentially of other expression control elements. It is particularly advantageous to incorporate stabilizing sequence(s), e.g., intron sequence(s), preferably the first intron of the hCMV-IE (PCT Application No. WO89/01036), the intron II of the rabbit β-globin gene (van Ooyen et al., Science, 1979, 206, 337-344).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit α-globin gene or the poly(A) signal of the SV40 virus.

According to an advantageous embodiment of the invention, the expression vector comprises the polynucleotides encoding the signal peptide of IGF1 and the propeptide GHRH deleted of the propeptide N-terminus (corresponding to 31-106 AA). According to another advantageous embodiment of the invention, the expression vector comprises the polynucleotides encoding the signal peptide of IGF1 and the mature GHRH (corresponding to 31-74 AA).

According to another embodiment of the invention, the expression vectors are expression vectors used for the in vitro expression of proteins in an appropriate cell system. The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods.

Host cells that can be used in the present invention include, but are not limited to, muscle cells, keratinocytes, myoblasts, Chinese Hamster ovary cells (CHO), vero cells, BHK21, sf9 cells, and the like. It is understood to one of skill in the art that conditions for culturing a host cell varies according to the particular gene and that routine experimentation is necessary at times to determine the optimal conditions for culturing canine GHRH depending on the host cell. For example, the vector encoding canine GHRH can be transformed into myoblasts (which can be obtained from muscle tissue from the animal in need of treatment), and the transformed myoblasts can be transplanted to the animal. As a result, myoblasts genetically engineered to express recombinant canine GHRH can secrete the hormone into the animal's blood. In another example, keratinocytes can also be transformed with a vector encoding GHRH and transplanted into the animal, resulting in secretion of canine GHRH into circulation.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

In an advantageous embodiment, the invention provides for the administration of a therapeutically effective amount of a formulation for the delivery and expression of a canine GHRH in a target cell. Determination of the therapeutically effective amount is routine experimentation for one of ordinary skill in the art. In one embodiment, the formulation comprises an expression vector comprising a polynucleotide that expresses canine GHRH and a pharmaceutically or veterinarily acceptable carrier, vehicle or excipient. In an advantageous embodiment, the pharmaceutically or veterinarily acceptable carrier, vehicle or excipient facilitates transfection and/or improves preservation of the vector or protein.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having

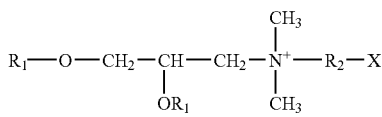

the following formula:

in which $R_1$ is a saturated or unsaturated straight-chain aliphatic radical having 12 to 18 carbon atoms, $R_2$ is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr J. P., 1994, Bioconjugate Chemistry, 5, 382-389), to form DMRIE-DOPE.

Advantageously, the plasmid mixture with the adjuvant is formed extemporaneously and advantageously contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is advantageously about 95:about 5 to about 5:about 95, more advantageously about 1:about 1, e.g., 1:1.

The DMRIE or DMRIE-DOPE adjuvant:plasmid weight ratio can be between about 50:about 1 and about 1:about 10, such as about 10:about 1 and about 1:about 5, and advantageously about 1:about 1 and about 1:about 2, e.g., 1:1 and 1:2.

In a specific embodiment, the pharmaceutical composition is directly administered in vivo, and the encoded product is expressed by the vector in the host. The methods of in vivo delivery a vector encoding GHRH (see, e.g., U.S. Pat. No. 6,423,693; patent publications EP 1052286, EP 1205551, U.S. patent publication 20040057941, WO 9905300 and Draghia-Akli et al., Mol Ther. 2002 December; 6 (6): 830-6; the disclosures of which are incorporated by reference in their entireties) can be modified to deliver the canine GHRH of the present invention to a dog. The in vivo delivery of a vector encoding the canine GHRH described herein can be accomplished by one of ordinary skill in the art given the teachings of the above-mentioned references.

Advantageously, the pharmaceutical and/or therapeutic compositions and/or formulations according to the invention comprise or consist essentially of or consist of an effective quantity to elicit a therapeutic response of one or more expression vectors and/or polypeptides as discussed herein; and, an effective quantity can be determined from this disclosure, including the documents incorporated herein, and the knowledge in the art, without undue experimentation.

In the case of therapeutic and/or pharmaceutical compositions based on a plasmid vector, a dose can comprise, consist essentially of or consist of, in general terms, about in 1 µg to about 2000 µg, advantageously about 50 µg to about 1000 µg and more advantageously from about 100 µg to about 800 µg of plasmid expressing GHRH. When the therapeutic and/or pharmaceutical compositions based on a plasmid vector is administered with electroporation the dose of plasmid is generally between about 0.1 µg and 1 mg, advantageously between about 1 µg and 100 µg, advantageously between about 2 µg and 50 µg. The dose volumes can be between about 0.1 and about 2 ml, advantageously between about 0.2 and about 1 ml. These doses and dose volumes are suitable for the treatment of canines and other mammalian target species such as equines and felines.

The therapeutic and/or pharmaceutical composition contains per dose from about $10^4$ to about $10^{11}$, advantageously from about $10^5$ to about $10^{10}$ and more advantageously from about $10^6$ to about $10^9$ viral particles of recombinant adenovirus expressing GHRH. In the case of therapeutic and/or pharmaceutical compositions based on a poxvirus, a dose can be between about $10^2$ pfu and about $10^9$ pfu. The pharmaceutical composition contains per dose from about $10^5$ to about $10^9$, advantageously from about $10^6$ to $10^8$ pfu of poxvirus or herpesvirus recombinant expressing GHRH.

The dose volume of compositions for target species that are mammals, e.g., the dose volume of canine compositions, based on viral vectors, e.g., non-poxvirus-viral-vector-based compositions, is generally between about 0.1 to about 2.0 ml, preferably between about 0.1 to about 1.0 ml, and more preferably between about 0.5 ml to about 1.0 ml.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Biojector or Vitajet apparatus (Bioject, Oregon, USA)). Another approach to administer plasmid compositions is to use electroporation (see, e.g. S. Tollefsen et al. Vaccine, 2002, 20, 3370-3378; S. Tollefsen et al. Scand. J. Immunol., 2003, 57, 229-238; S. Babiuk et al., Vaccine, 2002, 20,3399-3408; PCT Application No. WO99/01158). In another embodiment, the plasmid is delivered to the animal by gene gun or gold particle bombardment. In an advantageous embodiment, the animal is a vertebrate. In a more advantageous embodiment, the vertebrate is a dog.

The present invention relates to the use of a viral vector encoding and expressing canine GHRH, canine GHRH mature, canine pre-proGHRH, canine proGHRH, variant, analog or fragment to produce a pharmaceutical composition for the treatment of a disease condition. For example, the secretion of GH stimulated by the administration of GHRH according to the present invention may have a direct stimulatory effect on erythroid cells in an anaemic animal. However, other disease conditions that may benefit from administration of a GHRH composition include, but not limited to, cachexia, in particular, cachexia resulting from cancer, wound healing, bone healing, osteoporosis, obesity, and the like in a vertebrate. The vector expressing canine GHRH of the present invention has therapeutic utility in the treatment of cachexia (Bartlett et al Cancer 1994, 73, 1499-1504 and Surgery 1995, 117, 260-267) in chronic diseases such as cancer, due to growth hormone production abnormalities, in wound healing, bone healing, retardation of the aging process, osteoporosis and in anaemia (Sohmiya et al J. Endocrinol. Invest. 2000, 23, 31-36 and Clin. Endocrinl. 2001, 55, 749-754).

Intramuscular delivery of a plasmid encoding porcine GHRH has been demonstrated to stimulate growth hormone and IGF-I release in dogs to treat anemia and cachexia (see, e.g., Draghia-Akli et al., Mol Ther. 2002 December; 6 (6): 830-6). Chronic administration of GHRH has been demonstrated to promote bone healing in dogs (see, e.g., Dubreuil et al., Can J Vet Res. 1996 January; 60 (1): 7-13). It would be advantageous to administer the therapeutic canine GHRH vector of the present invention instead of the polyethylene rod surgical implant of Dubreuil et al. (Can J Vet Res. 1996 January; 60 (1): 7-13) to promote bone growth in an animal. Similarly, chornic administration of GHRH has been shown to promote wound healing in rats (see, e.g., Garrel et al., Surg Res. 1991 October; 51 (4): 297-302). Again, it would be advantageous to administer the therapeutic canine GHRH vector of the present invention instead of the slow-release pellet implant implant of Garrel et al. (Surg Res. 1991 October; 51 (4): 297-302) to promote wound healing in an animal.

The invention also relates to a method to stimulate the immune response of a vertebrate. In one embodiment, the vertebrate is a bird, cat, cow, dog, fish, goat, horse, human, mouse, monkey, pig, rat or sheep. In a more advantageous embodiment, the vertebrate is a dog.

Because lymphocytes express GH-IGF-I, GHRH and their respective receptors, administration of GHRH has been hypothesized to enhance immune cell function (see, e.g, Khorram et al., J Clin Endocrinol Metab. 1997 November; 82 (11): 3590-6). In humans, administration of GHRH analog to healthy elderly humans resulted in profound immune-enhancing effects and may provide therapeutic benefit in states of compromised immune function (see, e.g., Khorram et al., J Clin Endocrinol Metab. 1997 November; 82 (11): 3590-6). Overpexression of GHRH in transgenic mice led to significant stimulation of some parameters of immune function (see, e.g., Dialynas et al., J Clin Endocrinol Metab. 1997 November; 82 (11): 3590-6). In another mouse study, GHRH played a crucial role in the development of experimental autoimmune encephalomyelitis and may provide the basis for a therapeutic approach from protecting from autoimmune diseases (see, e.g., Ikushima et al., J. Immunol. 2003 Sep. 15; 171 (6): 2769-72). Since the above-mentioned studies suggest that GHRH enhances immune cell function, administration of the therapeutic canine GHRH vector of the present invention would be advantageous for stimulation of an immune response in a vertebrate.

The invention will now be further described by way of the following non-limiting examples.

EXAMPLES

Example 1

Hypothalamus was taken from a dog and was immediately frozen in liquid nitrogen. Total RNAs were extracted from the tissue using a kit from QIAGEN (Rneasy Mini Protocol for Isolation of Total RNA Catalog ref. 74104). The cells from the hypothalami were dissociated with a Potter Dounce in 600 µl of denaturing solution from the kit. This solution contained guanidinium isothiocyanate and beta-mercaptoethanol. The tissue homogenate was centrifuged 5 minutes at 14000 RPM (rotations per minute) to remove debris. 600 µl of a 70% ethanol solution was added and the mixture was loaded onto a Rneasy colomn and centrifuged 15 seconds at 10000 RPM. The column was rinsed two times with the RW1 buffer provided with the kit. The RNA was eluted with 50 µl RNAse-free buffer after centrifugation 1 minute at 14000 RPM.

The cDNAs were synthesized in 20 [α]reaction mixture containing 5 mM $MgCl_2$, 20 mM Tris HCl pH 8.3, 100 mM KCl, 1 mM DTT, 1 mM each dNTP, 20 units RNAse inhibitor, 50 units Moloney murine leukemia virus reverse transcriptase, 2.5 µM random hexanucleotide primers and 2 µl of total hypothalamic RNA. The reverse transcription step was done with the following cycle: 23° C. for 5 minutes, 42° C. for 20 minutes, 99° C. for 5 minutes and 10° C. for 5 minutes.

The cDNAs pool was amplified by Polymerase Chain Reaction (PCR) using the following oligonucleotides for the reaction:

```
NB151 (18 mer)
5'-ATGCYRCTCTGGGTGYTC-3'          (SEQ ID NO:5)

NB152 (17 mer)
5'-TCATCCYTGGGAGTTCC-3'           (SEQ ID NO:6)

NB153 (21 mer)
5'-GCTACCGGAAGGTKCTGGGCC-3'       (SEQ ID NO:7)

NB154 (21 mer)
5'-GGCCCAGMACCTTCCGGTAGC-3'       (SEQ ID NO:8)
``` wherein Y is C or T, R is A or G, K is G or T, M is A or C.

The oligonucleotides NB 151 and NB 154 were used to amplify a 136 base pairs (bp) fragment corresponding to the 5' end of the GHRH gene. NB 152 and NB 153 oligonucleotides were used to amplify an overlapping 206 bp fragment corresponding to the 3' end of the GHRH gene.

100 µl reaction mixture contains 20 µl cDNA mixture, 2.5 units DNA polymerase (J. Cline et al. Nucl. Acid Res. 1996, 24, 3546-3551 and H. Hogrefe et al. Proc. Natl. Acad. Sci. U.S.A 2002, 99, 596-601), 50 mM Tris HCl pH 8.2, 0.5 µg each oligonucleotide (NB151/NB154 or NB152/NB153). The amplification was carried out with 35 cycles: 94° C. for 30 seconds, 55° C. for 30 seconds, 72° C. for 1 minute, followed at the end by a 10 minutes extension at 72° C.

In order to obtain the nucleotide sequence of the 5' and 3' ends of the GHRH mRNA, the 5' and 3' ends of the cDNAs were amplified according a RACE protocol. For the 5' end a 5 µl mixture containing 3 µl of total hypothalamic RNA, 2 µM primer oligo dT 5'-CDS, 2 µM Smt oligonucleotide was heated at 70° C. and chilled on ice for denaturation. A 10 µl mixture reaction containing 5 µl of the denatured RNA with oligonucleotides, 50 mM Tris HCl pH 8.3, 75 mM KCl, 6 mM $MgCl_2$, 2 mM DTT, 1 mM each dNTP, 100 units reverse transcriptase was incubated 90 minutes at 42° C. and then diluted 1:10 in a buffer 10 mM Tricine-KOH pH 8.5, 1 mM EDTA. 2.5 µl aliquot was used for amplification in a 50 µl reaction mixture containing also 0.04 µM Universal primer, 0.2 µM NB 154 oligonucleotide, 40 mM Tricine-KOH pH 8.7, 15 mM KOAc, 3.5 mM $Mg(OAc)_2$, 3.75 µg/ml BSA, 0.005% Tween 20®, 0.005% Nonidet-P40, 0.2 µM each dNTP, 2.5 units Taq DNA polymerase. The amplification was carried out with 5 cyclation is carried out with 5 cycl 3 minutes and 30 cycles 94° C. for 30 seconds, 65° C. for 3 minutes, 72° C. for 3 minutes. A 239 bp fragment was obtained.

```
Smt (30 mer)
5'-AAGCAGTGGTATCAACGCAGAGTACGCGGG-3' (SEQ ID NO:9)
```

Oligo dT 5'-CDS 5'-(T)25N$_{-1}$N-3', wherein N$_{-1}$ is A, C or G and N is A, C, G or T.

```
Universal primer
5'-CTAATACGACTCACTATAGGGCAAGCAGTGGTATCAACGCAGAGT-3'    (SEQ ID NO:10)
```

For the 3' end the procedure is the same as described above except the 5 μl mixture containing only 3 μl of total hypothalamic RNA, 2 μM SMART (Clontech Laboratories, Palo Alto, Calif.) oligonucleotide and the 50 μl reaction mixture for PCR containing 2.5 μl aliquot of diluted cDNA, 0.04 μM universal primer mix, 0.2 μM NB153 oligonucleotide, 50 mM Tris HCl pH 8.3, 75 mM KCl, 6 mM MgCl2, 3.75 μg/ml BSA, 0.005% Tween 20®, 0.005% Nonodet-P40, 0.2 μM each dNTP, 2.5 units Taq DNA polymerase. A 386 bp fragment was obtained.

SMART (57 mer) 5'-AAGCAGTGGTATCAACGCA-GAGTAC(T)30N$_{-1}$N-3' (SEQ ID NO: 11), wherein N$_{-1}$ is A, C or G and N is A, C, G or T.

The PCR amplified fragments were cloned directly into an appropriate plasmid. *E. coli* colonies were screened by colony lift hybridization. The plasmids with GHRH cDNA were identified using the NB 155 probe labeled with alkaline phosphatase, corresponding to plasmids pCR11 NB 151/154 and pCR11 NB 152/153.

NB155 (50 mer) 5'-GCCATCTTCACYAACARCTACCG-GAAGGTBCTGGGCCAGCTVTCYGCCCG-3' (SEQ ID NO: 12), wherein Y is C or T, R is A or G, B is C or G or T, V is A or C or G.

The clones were sequenced. The nucleotide sequence encoding the canine pre-proGHRH comprising 321 bp is the following:

```
5'-ATGCCACTCT GGGTGTTCTT                                    (SEQ ID NO:3)
CCTGGTGATC CTCACCCTCA GCAGTGGCTC CCACTCTTCC CCGCCATCCC
TGCCCATCAG AATCCCTCGG TATGCAGACG CCATCTTCAC CAACAGCTAC
CGGAAGGTGC TGGGCCAGCT GTCCGCCCGC AAGCTCCTGC AGGACATCAT
GAGCCGGCAG CAGGGAGAGA GAAACCGGGA GCAGGAGCA AAGGTACGAC
TCGGCCGTCA GGTGGACAGT CTGTGGGCAA GCCAAAAGCA GATGGCATTG
GAGAACATCC TGGCATCCCT GTTACAGAAA CGCAGGAACT CCCAAGGATG A-3'.
```

The corresponding amino acid sequence is the following: H-MPLWVFFLVI LTLSSGSHSS PPSLPIRIPR YADAIFT-NSY RKVLGQLSAR KLLQDIMSRQ QGERNREQGA KVRLGRQVDS LWASQKQMAL ENILASLLQK RRN-SQG-OH (SEQ ID NO: 1). The signal peptide spans from amino acid 1 to amino acid 20; the mature GHRH spans from amino acid 31 to amino acid 74.

Example 2

The polynucleotide encoding the canine GHRH is obtained by RT-PCR from the total hypothalamic RNA using the NB 184 and NB 185 oligonucleotides and the DNA Polymerase (J. Cline et al. 1996 and H. Hogrefe et al. 2002).

NB 184 (33 mer): 5'-TTTCGCGGATCCTATGCA-GACGCCATCTTCACC-3' (SEQ ID NO: 13) (contains a BamH I site on its 5' end)

NB185 (35 mer): 5'-AAAGCTCTAGATCAACGGC-CGAGTCGTACCTTTGC-3' (SEQ ID NO: 14) (contains a Xba I site on its 5' end).

The amplification is carried out with 1 cycle for reverse transcription step 42° C. for 15 minutes, 95° C. for 5 minutes, 4° C. for 5 minutes and 30 cycles for PCR step 95° C. for 45 seconds, 55° C. for 45 seconds, 72° C. for 1 minute.

The PCR product (164 pb) is purified by phenol-chloroform extraction and subsequently digested by BamH I and Xba I to generate a BamH I/Xba I of 147 bp (fragment A).

The plasmid pAB110 is derived from pVR1020 plasmid (Vical Inc) by insertion of a polylinker (BamH I, Not I, EcoR I, EcoR V, Xba I, Pml I, Pst I, Bgl II) corresponding to the PB326 and PB329 oligonucleotides after BamH I/Bgl II digestion of the plasmid.

```
PB326 (40 mer)
5'-GATCTGCAGCACGTGTCTAGAGGATATCGAATTCGCGGCC-3'    (SEQ ID NO:15)
```

```
PB329 (40 mer)
5'-GATCCGCGGCCGCGAATTCGATATCCTCTAGACACGTGCT-3'    (SEQ ID NO:16)
```

Plasmid pAB110 is linearized by a BamH I/Xba I digestion to generate fragment B (5055 bp).

Fragments A and B are subsequently purified and are ligated to generate plasmid pNB179 (5202 bp) (FIG. 1).

Example 3

The plasmid pCR11 NB151/154 is first digested by EcoRI. The EcoRI fragment (167 bp) is purified and finally digested by BsaWI to generate a EcoRI-BsaWI fragment (143 bp). The plasmid pCR11 NB 152/153 is fisrt digested by EcoRI. The EcoRI fragment (235 bp) is purified and finally digested by BsaWI to generate a BsaWI-EcoRI fragment (220 bp).

These two fragments are subsequently purified and cloned into plasmid pCR11 NB151/154 linearized by EcoRI to generate the final plasmid pCR11 NB 151/152 (4295 bp).

Example 4

Construction of pNB$^2$09 is based on a pVR1012 plasmid (Vical Inc.) encoding the canine GHRH precursor (106 amino acid polypeptide).

The DNA fragment corresponding to the cGHRH gene, with additional SalI and XbaI sites at respectively, the 5' and 3' ends, is amplified by PCR using primers NB361 and NB360, the plasmid pCRIINB151/152 as a template and the DNA Polymerase.

NB360 (30 mer): 5'-AAAGCTCTAGATCATCCTTGG-GAGTTCCTG-3' (SEQ ID NO: 17) (contains a XbaI site on its 5' end)

NB361 (31 mer): 5'-TTTACGCGTCGACATGCT-GCTCTGGGTGTTC-3' (SEQ ID NO: 18) (contains a SalI site on its 5' end)

The PCR fragment (345 bp) was purified by phenol-chloroform extraction and subsequently digested by SalI and XbaI to generate fragment A (327 bp).

Plasmid pVR1012 is linearized by a SalI/XbaI digestion to generate fragment B (4880 bp).

Fragments A and B are subsequently purified and are ligated to generate plasmid pNB209 (5207 bp). FIG. 2 shows the plasmid map and the encoded ORF of pNB209.

Example 5

Construction of plasmids pNB210/pNB211/pNB212/pNB213: pAB110-derived plasmids containing modified GHRH genes, encoding hybrid proteins containing the eukaryotic tPA leader peptide fused to the GHRH propeptide.

The DNA fragment corresponding to the tPA (1-23 AA) with additional SalI and Eco47III sites at, respectively, the 5' and 3' ends, is obtained by PCR using primers NB355 and NB356, plasmid pAB110 as a template and the DNA Polymerase (J. Cline et al. 1996 and H. Hogrefe et al. 2002).

NB355 (20 mer): 5'-CCGTCGTCGACAGAGCTGAG-3' (SEQ ID NO: 19) (contains a SalI site on its 5' end)

NB356 (24 mer): 5'-AAAAGCGCTGGGCGAAACGAA-GAC-3' (SEQ ID NO: 20) (contains a Eco47III site on its 5' end)

The PCR fragment (184 bp) is purified by phenol-chloroform extraction and subsequently digested by SalI and Eco47III to generate fragment A (172 bp).

The DNA fragment corresponding to the tPA (1-28 AA) with additional SalI and NaeI sites at, respectively, the 5' and 3' ends, is obtained by PCR using primers NB355 and NB357, the plasmid pAB110 as a template and the DNA Polymerase.

NB355 (20 mer): 5'-CCGTCGTCGACAGAGCTGAG-3' (SEQ ID NO: 19) (contains a SalI site on its 5' end)

NB357 (42 mer): 5'-AAAGCCGGCATGGATTTTCCTG-GCTGGGCGAAACGAAGAC TGC-3' (SEQ ID NO: 21) (contains the 5 AA additional of the tPA leader peptide and a NaeI site on its 5' end).

The PCR fragment (199 bp) is purified by phenol-chloroform extraction and subsequently digested by SalI and NaeI to generate fragment B (187 bp).

The DNA fragment corresponding to the deletion (1-19 AA) GHRH with additional NlaIV and XbaI sites at, respectively, the 5' and 3' ends, is obtained by PCR using primers NB358 and NB360, the plasmid pCR11 NB151/152 as a template and the DNA Polymerase.

NB358 (21 mer): 5'-TTTGGTTCCCCGCCATCCCTG-3' (SEQ ID NO: 22) (contains a NlaIV site on its 5' end)

NB360 (30 mer): 5'-AAAGCTCTAGATCATCCTTGG-GAGTTCCTG-3' (SEQ ID NO: 17) (contains a XbaI site on its 5' end).

The PCR fragment (281 bp) is purified by phenol-chloroform extraction and subsequently digested by NlaIV and XbaI to generate fragment C (265 bp).

The DNA fragment corresponding to the deletion (1-20 AA) GHRH with additional StuI and XbaII sites at, respectively, the 5' and 3' ends, is obtained by PCR using primers NB359 and NB360, the plasmid pCR11 NB151/152 as a template and the DNA Polymerase.

NB359 (24 mer): 5'-TTTAGGCCTCCATCCCTGC-CCATC-3' (SEQ ID NO: 23) (contains a StuI site on its 5' end)

NB360 (30 mer): 5'-AAAGCTCTAGATCATCCTTGG-GAGTTCCTG-3' (SEQ ID NO: 17) (contains a XbaI site on its 5' end)

The PCR fragment (278 bp) is purified by phenol-chloroform extraction and subsequently digested by StuI and XbaI to generate fragment D (262 bp).

Plasmid pVR1012 is linearized by a SalI/XbaI digestion to generate fragment E (4880 bp).

Figure 3:
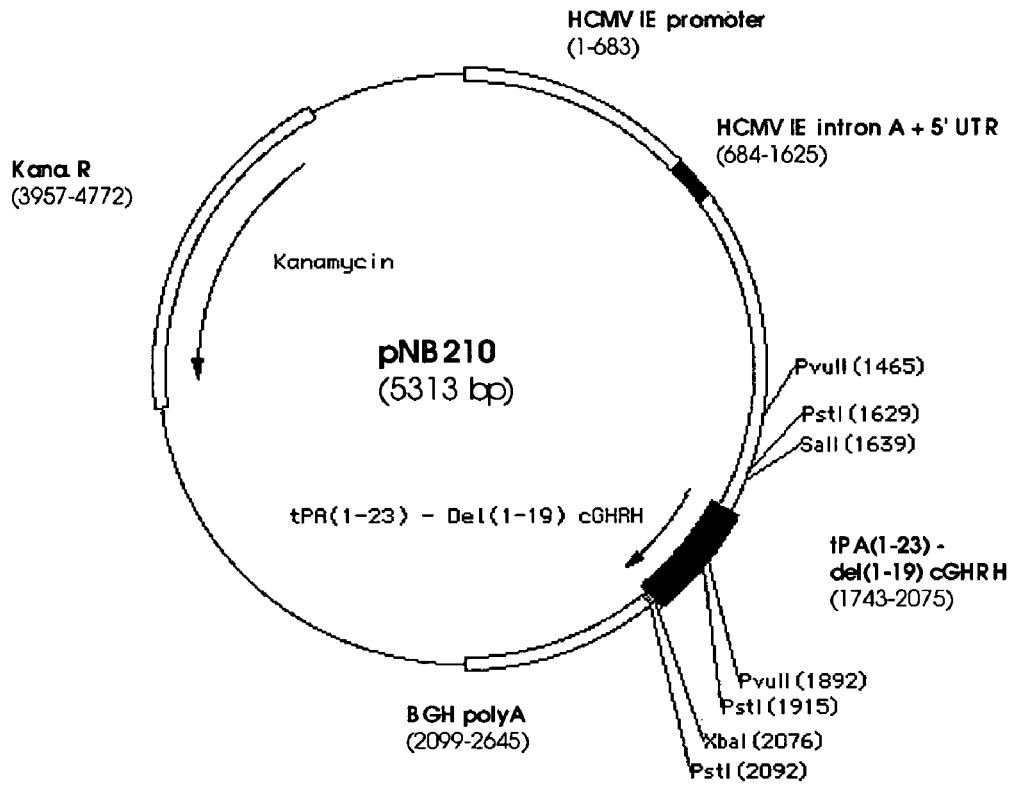
FIG. 3 depicts the plasmid map and the encoded ORF of pNB210. The nucleotide sequence of the encoded ORF is SEQ ID NO: 28 and the amino acid sequence of the encoded ORF is SEQ ID NO: 29.

Fragments E, A and C are subsequently purified and are ligated to generate plasmid pNB$^2$10 (5313 bp). FIG. 3 shows the plasmid map and the encoded ORF of pNB210.

Fragment E, A and D are subsequently purified and are ligated to generate plasmid pNB211 (5310 bp). FIG. 4 shows the plasmid map and the encoded ORF of pNB211.

Fragment E, B and C are subsequently purified and are ligated to generate plasmid pNB212 (5331 bp). FIG. 5 shows the plasmid map and the encoded ORF of pNB212.

4Fragment E, B and D are subsequently purified and are ligated to generate plasmid pNB213 (5328 bp). FIG. 6 shows the plasmid map and the encoded ORF of pNB213.

Example 6

Construction of Plasmids pNB214/pNB215

Construction of plasmids pNB214/pNB215: pAB 110-derived plasmids containing modified GHRH genes, encoding hybrid proteins containing the human tPA fused to the canine GHRH mature peptide.

The DNA fragment corresponding to the peptide (31-74 AA) GHRH with additional BstI 1071 and XbaII sites at, respectively, the 5' and 3' ends, is obtained by PCR using primers NB362 and NB363, the plasmid pCR11 NB151/152 as a template and the DNA Polymerase (J. Cline et al. 1996 and H. Hogrefe et al. 2002).

NB362 (27 mer): 5'-TTTGTATACGCAGACGCCATCT-TCACC-3' (SEQ ID NO: 24) (contains a BstI 107II site on its 5' end)

NB363 (32 mer): 5'-AAAGCTCTAGATCAGAGTCG-TACCTTTGCTCC-3' (SEQ ID NO: 25) (contains a XbaI site on its 5' end)

The PCR fragment (152 bp) is purified by phenol-chloroform extraction and subsequently digested by BstI 107II and XbaI to generate fragment F (136 bp).

Figure 7:
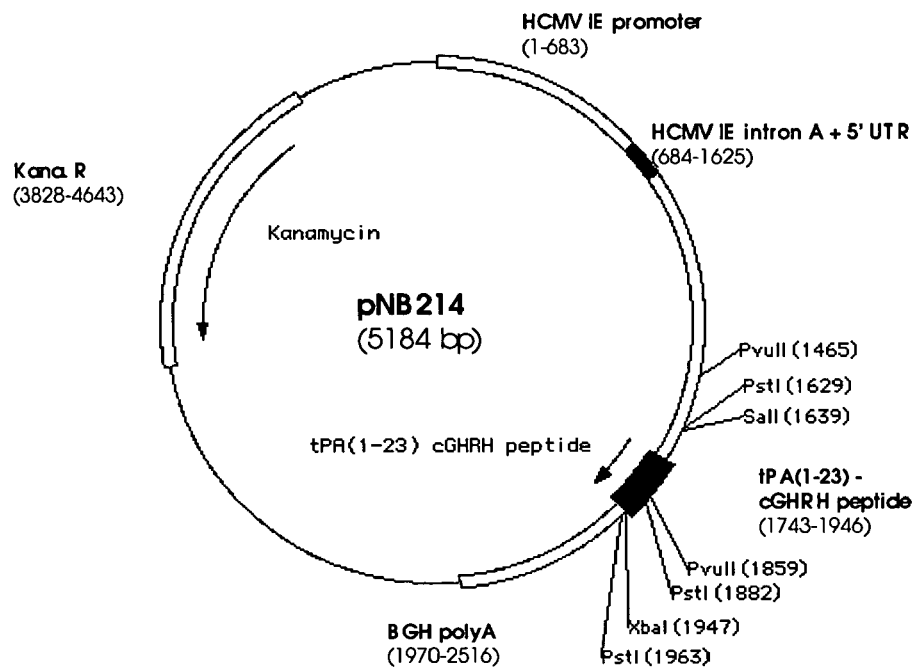
FIG. 7 depicts the plasmid map and the encoded ORF of pNB214. The nucleotide sequence of the encoded ORF is SEQ ID NO: 36 and the amino acid sequence of the encoded ORF is SEQ ID NO: 37.

Fragment E, A and F are subsequently purified and are ligated to generate plasmid pNB214 (5184 bp). FIG. 7 shows the plasmid map and the encoded ORF of pNB214.

Fragment E, B and F are subsequently purified and are ligated to generate plasmid pNB215 (5202 bp). FIG. 8 shows the plasmid map and the encoded ORF of pNB215.

Fragment E, A and B are described in example 5.

Example 7

The canine pre-pro GHRH nucleotide sequence is optimized by removing cryptic splice sites, by adapting the codon usage to the one of *Canis familiaris*, by introducing Kozak consensus sequence in order to improve expression. Such a modified gene is obtained by synthesis: SEQ ID NO: 40.

Construction of pNB216: is based on a pVR1012 plasmid (Vical Inc.) encoding the canine GHRH optimized precursor (106 amino acid polypeptide) SEQ ID NO: 40.

The plasmid pCR-Script Amp-GHRH (Stratagene, Lajolla, Calif., USA) inserting the optimized canine pre-proGHRH gene is digested with SalI and XbaI to generate a SalI-XbaI fragment (336 bp) and plasmid pVR1012 is linearized by a SalI/XbaI digestion to generate fragment E (4880 bp). These two fragments are subsequently purified and ligated to generate the final plasmid pNB216 (5216 bp).

Example 8

Construction of plasmids pNB217/pNB218: pABI 10-derived plasmids containing modified GHRH genes, encoding hybrid proteins containing the eukaryotic tPA leader peptide fused to the GHRH propeptide optimized.

The DNA fragment corresponding to the deletion (1-20 AA) GHRH optimized with additional NlaIV and XbaI sites at, respectively, the 5' and 3' ends, is obtained by PCR using primers NB364 and NB365, the pCR-Script Amp-GHRH plasmid as a template and the DNA Polymerase.

NB364 (24 mer): 5'-TTT GGCCCCCCCAGCCTGCCCATC-3' (SEQ ID NO: 45) (contains a NlaIV site on its 5' end)

NB365 (33 mer): 5'-AAAGC TCTAGATTATCAGCCCTGGCTGTTCCGC-3' (SEQ ID NO: 46) (contains a XbaI site on its 5' end)

The PCR fragment (281 bp) is purified by phenol-chloroform extraction and subsequently digested by NlaIV and XbaI to generate fragment G (265 bp).

Plasmid pVR1012 is linearized by a SalI/XbaI digestion to generate fragment E (4880 bp).

Fragments E, A and G are subsequently purified and are ligated to generate plasmid pNB217 (5313 bp). FIG. 10 shows the plasmid map and the encoded ORF of pNB217.

Fragment E, B and G are subsequently purified and are ligated to generate plasmid pNB218 (5328 bp). FIG. 11 shows the plasmid map and the encoded ORF of pNB218.

Fragment A and B are described in example 5.

Example 9

Construction of plasmids pNB219/pNB220: pAB110-derived plasmids containing modified GHRH genes, encoding hybrid proteins containing the human tPA fused to the canine GHRH mature peptide optimized.

The DNA fragment corresponding to the peptide (31-74 AA) GHRH optimized with additional BstI 1071 and XbaI sites at, respectively, the 5' and 3' ends, is obtained by PCR using primers NB366 and NB367, the plasmid pCR11 NB151/152 as a template and the DNA Polymerase (J. Cline et al. 1996 and H. Hogrefe et al. 2002).

NB366 (27 mer): 5'-TTT GTATACGCCGACGCCATCTTCACC-3' (SEQ ID NO: 47) (contains a BstI 1071 site on its 5' end)

NB367 (32 mer): 5'-AAAGC TCTAGATCACAGCCGCACT=TGGCGCC-3' (SEQ ID NO: 48) (contains a XbaI site on its 5' end)

The PCR fragment (152 bp) is purified by phenol-chloroform extraction and subsequently digested by BstI 1071 and XbaI to generate fragment H (136 bp).

Figure 12:
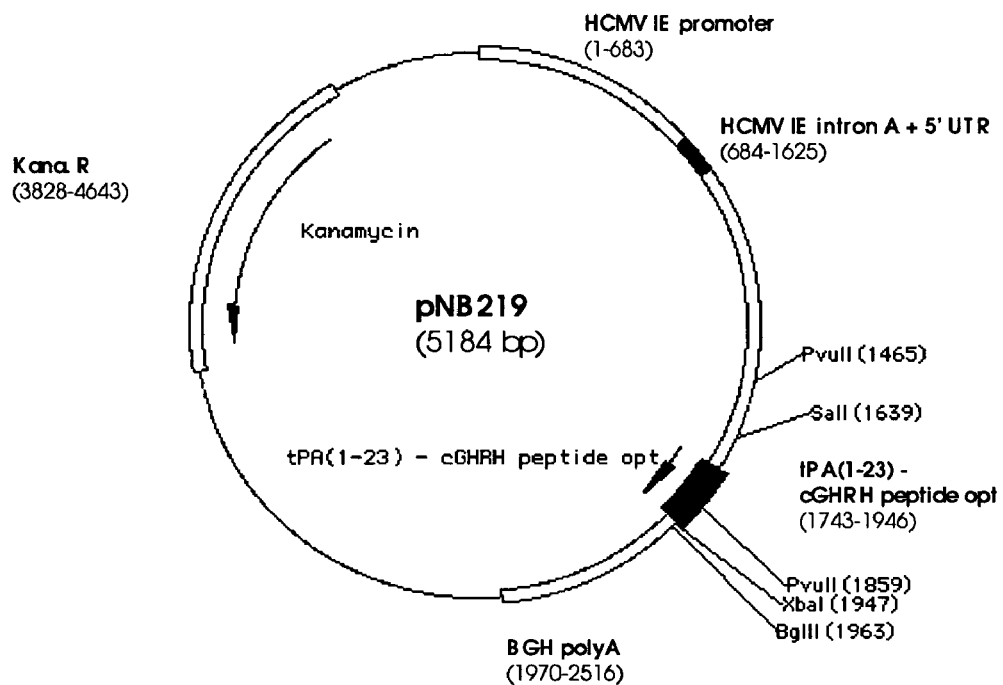
FIG. 12 depicts the plasmid map and the encoded ORF of pNB219. The nucleotide sequence of the encoded ORF is SEQ ID NO: 43 and the amino acid sequence of the encoded ORF is SEQ ID NO: 37.

Fragment E, A and H are subsequently purified and are ligated to generate plasmid pNB219 (5184 bp). FIG. 12 shows the plasmid map and the encoded ORF of pNB219.

Figure 13:
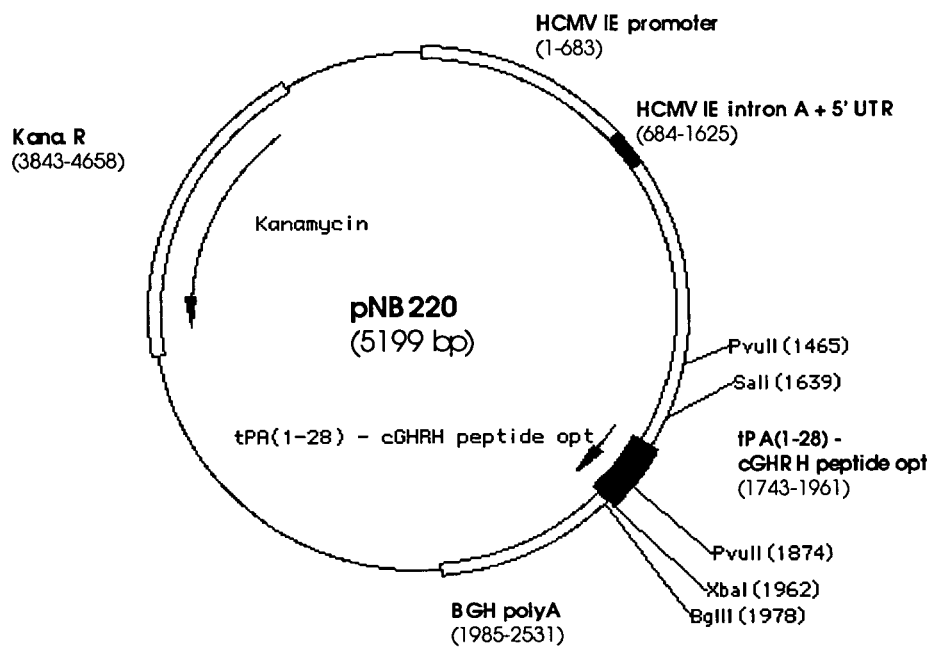
FIG. 13 depicts the plasmid map and the encoded ORF of pNB220. The nucleotide sequence of the encoded ORF is SEQ ID NO: 44 and the amino acid sequence of the encoded ORF is SEQ ID NO: 39.

Fragment E, B and H are subsequently purified and are ligated to generate plasmid pNB220 (5199 bp). FIG. 13 shows the plasmid map and the encoded ORF of pNB220.

Fragment A and B are described in example 5.

Example 10

A method for low voltage electroporation for DNA uptake and expression in an animal can be adapted from Example 2 of U.S. patent publication 20040057941, the disclosure of which is incorporated by reference in its entirety. The method described herein can be modified to deliver the plasmid of the present invention without undue experimentation.

Direct intra-muscular plasmid DNA injection followed by electroporation is a method for the local and controlled delivery of plasmid DNA into skeletal muscle. It has the advantage that is uses low plasmid quantities (as low as 0.1 mg), rather than the high quantities typically used with passive delivery modalities. Although not wanting to be bound by theory, the mechanism of the increased plasmid uptake by electroporation probably occurs through newly created membrane pores with or without protein active transport. Although not wanting to be bound by theory, the degree of permeabilization of the muscle cells is dependent on the electric field intensity, length of pulses, shape and type of electrodes (Bureau et al., Biochim Biophys Acta. 2000 May 1; 1474 (3): 353-9 and Gilbert et al., Biochim Biophys Acta. 1997 Febaury 11; 1334 (1): 9-14.), and cell size (Somiari et al., Mol Ther. 2000 September; 2 (3): 178-87). Classical electrode configuration, plates or a pair of wire electrodes placed 4 mm apart were shown to be effective in rodents, but in large mammals as pigs or humans the increased resistance of the skin, the thickness of the subcutaneous fat tissue, and the concern for tissue damage if the intensity of the electric field would be proportionally increased, make these types of electrodes unpractical. The porcine or dog muscle fibers are quite large and consequently more suitable for electropermeabilization than rodent muscle. In this report, we show that a single injection various dosages of GHRH or analog nucleic acid sequences followed by electroporation with intramuscular applicators, in a large mammal is sufficient to produce therapeutic plasma hormone levels, with biologically significant effects that can treat anemia, reverse wasting, allow the subject to gain weight, and extend life expectancy of the chronically ill.

The pSP-HV-GHRH system (a vector expressing porcine GHRH) was delivered to the left tibialis anterior muscle of healthy dogs via in vivo electroporation. A group of 4 dogs (2 males and 2 females) were used as controls and 3 groups of 8 dogs (4 males and 4 females) were injected with the pSP-HV-GHRH system. The dogs were injected with vehicle alone (control), or 200 mcg, or 600 mcg or 1000 mcg of pSP-HV-GHRH followed by needle electroporation. An indication of increased systemic levels of GHRH and GH is an increase in serum IGF-I concentration. Therefore, following 28 days post injection blood serum was collected from the dogs were injected with vehicle alone (control), or 200 mcg, or 600 mcg or 1000 mcg of pSP-HV-GHRH and IGF-I levels were determined. The IGF-I levels for dogs injected with 600 mcg were 3-fold higher than the control (vehicle alone) treated animals (FIG. 2). The increase in IGF-I levels was statistically significant (p<0.046). Although animals injected with 200 mcg and 1000 mcg of plasmid showed higher IGF-I levels than controls, the IGF-I levels were lower than animals injected with 600 mcg. Increased IGF-I levels corresponding to higher GHRH levels are in agreement with other studies that utilized recombinant porcine GH ("pGH") in dogs. For example, there were dose-related increased serum IGF-I levels (approximately 2-10-fold) that correlated with the elevated serum GH levels in pGH-treated dogs.

Although not wanting to be bound by theory, growth hormone releasing hormone (GHRH) stimulates the production and release from the anterior pituitary of growth hormone (GH), which in turn stimulates the production of IGF-I from the liver and other target organs. Thus, an indication of increased systemic levels of GHRH and GH is an increase in serum IGF-I concentration. The level of serum IGF-I in healthy dogs injected with 200, 600 and 1000 mcg of pSP-HV-GHRH were all higher 28 days post-injection when compared to the pre-injection values. Dogs injected with 600 mcg pSP-HV-GHRH showed the highest statistically significant increase (e.g. greater than 90%, p<0.046) in IGF-I levels, which indicates that 600 mcg may be the optimal concentration for healthy dogs.

Example 11

Construction of plasmids pNB240, pNB239 and pNB244

Construction of pNB240 is based on a pVR1012 plasmid (Vical Inc.) comprising a modified GHRH gene, encoding a hybrid protein containing the pre-proGHRH deleted of the propeptide C-terminus and fused to the c-myc epitope tag.

Constructions of pNB239 and pNB244 are based on a pVR1012 plasmid (Vical Inc.) comprising a modified GHRH gene, encoding a hybrid protein containing the equine IGF1 (Insulin-like Growth Factor 1) peptide signal sequence (SSIGF1, disclosed in Genbank under the accession numbers U28070 (24-48 AA) and U85272) fused to the modified GHRH and fused to the c-myc epitope tag.

The DNA fragment encoding the pre-proGHRH deleted of the propeptide C-terminus (corresponding to 1-74 AA) and fused to the c-myc epitope tag, with additional XbaI site at the 3' end, is amplified by PCR using primers PBO91 and NB412, the plasmid pNB209 (see example 4) as a template and the DNA Polymerase.

PB091 (22 mer): 5'-CCAGACATAATAGCTGACAGAC-3' (SEQ ID NO: 51)

NB412 (68 mer): 5'-AAAGCTCTAGATTAGAGATC-CTCTTCTGAGATAAGCTTTTGTTCGAGTCGTACCTT TGCTCCTTGCTC-3' (contains the c-myc epitope tag and a XbaI site on its 3' end) (SEQ ID NO: 52)

The PCR fragment (338 bp) was purified by phenol-chloroform extraction and subsequently digested by SalI and XbaI to generate fragment A (261 bp).

The equine pre-pro IGF1 nucleotide sequence is optimized by removing cryptic splice sites, by adapting the codon usage, by introducing a Kozak consensus sequence before the start codon in order to improve expression. Such a modified gene is obtained by synthesis: SEQ ID NO: 65.

The plasmid pCR-Script Amp-eIGF1 (Stratagene, Lajolla, Calif., USA) comprising the optimized equine IGF1 gene is used as a template for PCR with primers NB393 and NB394 and the DNA Polymerase.

NB393 (38 mer): 5'-TTTGCGTCGACGCCACCATGCA-CATCATGAGCAGCAGC-3' (contains a SalI site on its 5' end) (SEQ ID NO: 66)

NB394 (38 mer): 5'-AAAGCTCTAGATTATCACATC-CGGTAGTTCTTGTTGCC-3' (contains a XbaI site on its 5' end) (SEQ ID NO: 67)

The PCR fragment (424 bp) is purified by phenol-chloroform extraction and subsequently digested by SalI and XbaI to generate fragment F (408 bp).

Plasmid pVR1012 is linearized by a SalI/XbaI digestion to generate fragment E (4880 bp).

Fragments E and F are subsequently purified and are ligated to generate plasmid pNB231 (5288 bp).

The DNA fragment corresponding to the equine SSIFG1 (1-25 AA of FIGS. 15-18), with additional NaeI site at the 3' end, is obtained by PCR using primers PB091 and NB398, plasmid pNB231 as a template and the DNA Polymerase (J. Cline et al. 1996 and H. Hogrefe et al. 2002).

PB091 (22 mer) (SEQ ID NO: 51)

NB398 (25 mer): 5'-AAAGCCGGCGGTGGCGCT-GCTGGTG-3' (contains a NaeI site on its 3' end) (SEQ ID NO: 53)

The PCR fragment (159 bp) is purified by phenol-chloroform extraction and subsequently digested by SalI and NaeI to generate fragment B (86 bp).

The DNA fragment corresponding to the GHRH mature peptide (31-74 AA) fused to the c-myc epitope tag, with additional BstI 1071 and XbaI sites at, respectively, the 5' and 3' ends, is obtained by PCR using primers NB362 and NB412, the plasmid pNB209 as a template and the DNA Polymerase.

NB362 (27 mer) (SEQ ID NO: 24)
NB412 (68 mer) (SEQ ID NO: 52)

The PCR fragment (182 bp) is purified by phenol-chloroform extraction and subsequently digested by Bstl 107I and XbaI to generate fragment C (166 bp).

The DNA fragment corresponding to the GHRH pro-peptide deleted of the propeptide C-terminus (20-74 AA) fused to the c-myc epitope tag, with additional NlaIV and XbaI sites at, respectively, the 5' and 3' ends, is obtained by PCR using primers NB358 and NB412, the plasmid pNB209 as a template and the DNA Polymerase.

NB358 (21 mer) (SEQ ID NO: 22)
NB412 (68 mer) (SEQ ID NO: 52)

The PCR fragment (215 bp) is purified by phenol-chloroform extraction and subsequently digested by Bstl 1071 and XbaI to generate fragment D (199 bp).

Plasmid pVR1012 is linearized by a SalI/XbaI digestion to generate fragment E (4880 bp).

Fragments E and A are subsequently purified and are ligated to generate plasmid pNB240 (5141 bp). FIG. 14 shows the plasmid map and the encoded ORF of pNB240.

Fragment E, B and C are subsequently purified and are ligated to generate plasmid pNB239 (5132 bp). FIG. 15 shows the plasmid map and the encoded ORF of pNB239.

Figure 16:
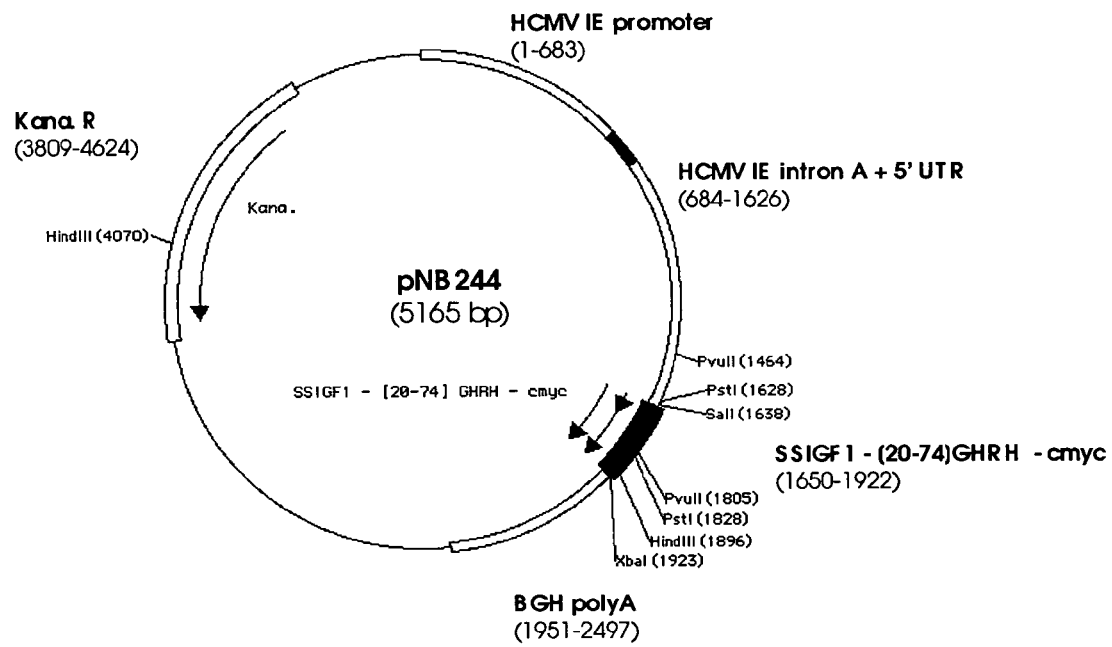
FIG. 16 depicts the plasmid map and the encoded ORF of pNB244. The nucleotide sequence of the encoded ORF is SEQ ID NO: 59 and the amino acid sequence of the encoded ORF is SEQ ID NO: 60.

Fragment E, B and D are subsequently purified and are ligated to generate plasmid pNB244 (5165 bp). FIG. 16 shows the plasmid map and the encoded ORF of pNB244.

The in vitro expressions of the fusion proteins encoded by pNB239, pNB240 and pNB2[44] were studied after transient transfection of CHO-KI cells (Chinese hamster ovary cells, available before the American Tissue Culture Collection ATCC under Cat. No. CCl-61), using Lipofectamin 2000. CHO-Ki cells at 90% confluency in 6 cm diameter plates were transfected with 5 μg plasmid and 10 μl lipofectamine each, according manufacturer's instructions. After transfection, cells were cultivated in MEM-glutamax medium containing 1% FCV (fetal calf serum) for 24 hours. Culture supernatants were harvested and concentrated 40 times by trichoroacetic acid precipitation of proteins. Cells were washed with PBS (phosphate-buffered saline), harvested by scraping, and lyzed using Laemmli SDS-PAGE loading buffer. Recombinant protein production and secretion were analyzed by submitting whole cell extracts and concentrated (40×) culture supernatants to SDS-PAGE and western blotting, using an anti-c-myc monoclonal antibody (Euromedex, France).

Plasmid pNB240 encodes a hybrid protein containing aminoacids 1 to 74 of the preproGHRH and fused to the c-myc epitope tag.

Plasmid pNB239 encodes a hybrid protein containing the equine IGF1 peptide signal sequence (SSIGF1) fused to the GHRH mature peptide (31-74 AA) and the c-myc epitope tag.

Plasmid pNB244 encodes a hybrid protein containing the equine IGF1 peptide signal sequence (SSIGF1) fused to the GHRH propeptide (20-74 AA) and the c-myc epitope tag.

Expression results are summarized in the Table 1. The three constructs lead to an expression product of 6.3 kDa in culture supernatants, which show correct maturation of the recombinant hormones.

TABLE 1

| pNB239 | | pNB240 | | pNB244 | |
|---|---|---|---|---|---|
| Cell extracts | Supernatants | Cell extracts | Supernatants | Cell extracts | Supernatants |
|  |  | Major 9.5 kDa | Major 9.5 kDa | Major 9.5 kDa | Minor 9.5 kDa |
|  |  | Minor 7.5 kDa | Minor 7.5 kDa | Major 7.5 kDa | Major 7.5 kDa |
| Major 6.3 kDa | Major 6.3 kDa |  | Minor 6.3 kDa |  | Minor 6.3 kDa |

Example 12

Construction of Plasmids pNB232 and pNB245

Constructions of pNB232 and pNB245 are based on a pVR1012 plasmid (Vical Inc.) comprising a modified GHRH gene, encoding a hybrid protein containing the equine IGF1 peptide sequence signal (SSIGF1, disclosed in Genbank under the accession numbers U28070 (24-48 AA) and U85272) fused to the modified GHRH.

The DNA fragment corresponding to the propeptide GHRH deleted of the propeptide N-terminus (corresponding to 31-106 AA) with additional Bstl 1071 and XbaI sites at, respectively, the 5' and 3' ends, is obtained by PCR using primers NB362 and NB421, the plasmid pNB209 (see example 4) as a template and the DNA Polymerase (J. Cline et al. 1996 and H. Hogrefe et al. 2002).

NB362 (27 mer) (SEQ ID NO: 24)
NB421 (36 mer): 5'-AAAGCTCTAGATTATCCTTGG-GAGTTCCTGCGTTTC-3' (contains a XbaI site on its 5' end) (SEQ ID NO: 54)

The PCR fragment (248 bp) is purified by phenol-chloroform extraction and subsequently digested by Bstl 1071 and XbaI to generate fragment G (232 bp).

Plasmid pVR1012 is linearized by a SalI/XbaI digestion to generate fragment H (4880 bp).

Figure 17:
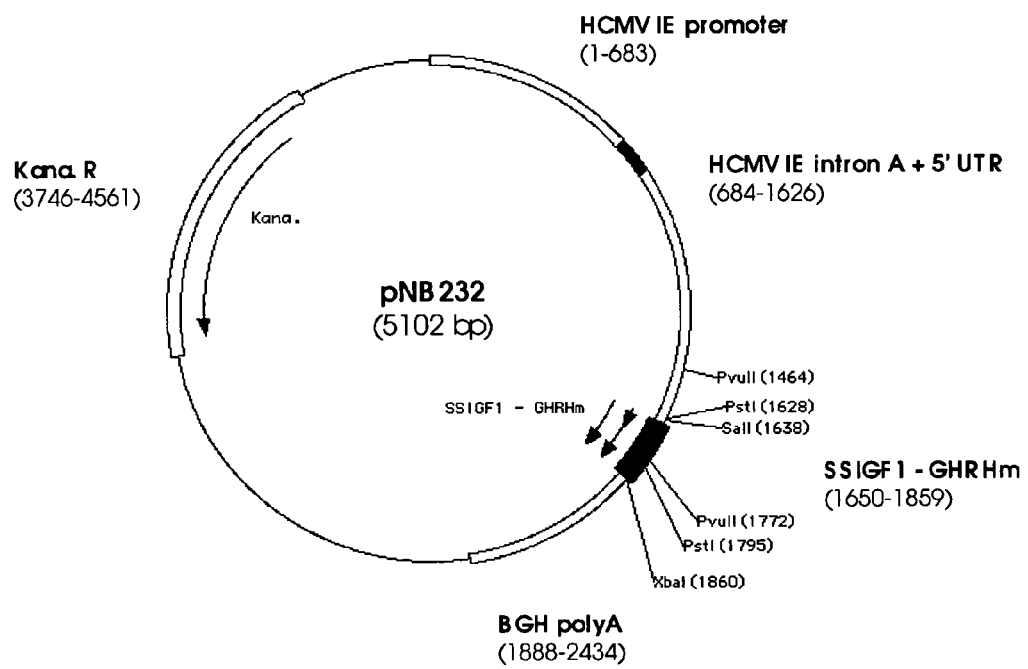
FIG. 17 depicts the plasmid map and the encoded ORF of pNB232. The nucleotide sequence of the encoded ORF is SEQ ID NO: 61 and the amino acid sequence of the encoded ORF is SEQ ID NO: 62.

Fragment H, B and F are subsequently purified and are ligated to generate plasmid pNB232 (5102 bp). FIG. 17 shows the plasmid map and the encoded ORF of pNB232.

Figure 18:
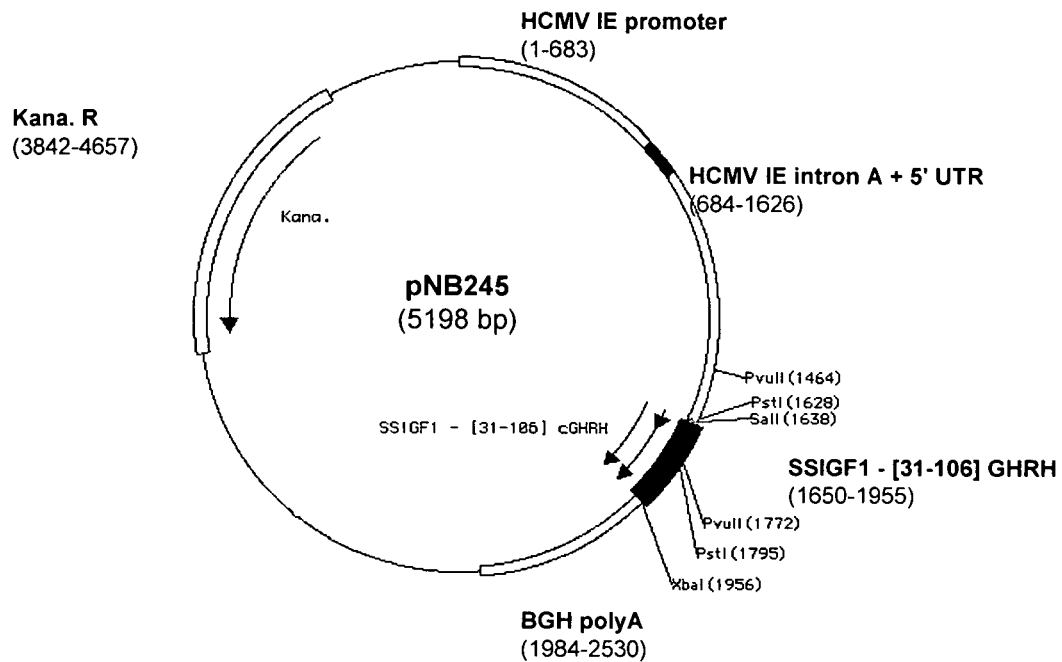
FIG. 18 depicts the plasmid map and the encoded ORF of pNB245. The nucleotide sequence of the encoded ORF is SEQ ID NO: 63 and the amino acid sequence of the encoded ORF is SEQ ID NO: 64.

Fragment H, B and G are subsequently purified and are ligated to generate plasmid pNB245 (5198 bp). FIG. 18 shows the plasmid map and the encoded ORF of pNB245.

The fragment B is described in example 11. The fragment F is described in example 6.

Having thus described in detail advantageous embodiments of the present invention, it is to be understood that the invention defined by the above paragraphs is not to be limited to particular details set forth in the above description as many apparent variations thereof are possible without departing from the spirit or scope of the present invention.

What is claimed is:

1. An expression vector for expressing a canine pro-GHRH deleted of the propeptide N-terminus comprising a polynucleotide operatively linked to a promoter and optionally to an enhancer, wherein the polynucleotide comprises (a) a polynucleotide encoding a canine proGHRH N-terminus deleted polypeptide having at least 95% sequence identity to amino acids 31 to 106 of SEQ ID NO: 1; or (b) a polynucleotide having at least 95% sequence identity to nucleotides 91 to 321 of SEQ ID NO:3 and encoding a canine proGHRH N-terminus deleted polypeptide; and (c) a polynucleotide encoding a secretory signal peptide sequence fused to the nucleotide base sequence from nucleotide 91 to nucleotide 321 of SEQ ID NO: 3;

wherein the canine pro-GHRH polypeptide deleted of the propeptide N-terminus, when expressed in vivo in a canine is able to be cellularly processed to mature canine GHRH with the ability to stimulate growth hormone secretion.

2. An expression vector for expressing a canine mature GHRH comprising a polynucleotide operatively linked to a promoter and optionally to an enhancer, wherein the polynucleotide comprises
  (a) a polynucleotide encoding a canine mature GHRH polypeptide having at least 95% sequence identity to SEQ ID NO: 2; or
  (b) a polynucleotide having at least 97% sequence identity to SEQ ID NO:4 and encoding a canine mature GHRH; and
  (c) a polynucleotide encoding a secretory signal peptide sequence for the secretion of the canine GHRH of SEQ ID NO: 4, fused to the nucleotide sequence of SEQ ID NO: 4;
  wherein the canine mature GHRH polypeptide, when expressed in vivo in a canine is able to be cellularly processed to mature canine GHRH with the ability to stimulate growth hormone secretion.

3. The expression vector of claim 1, wherein the signal peptide sequence fused to the nucleotide base sequence is an IGF-1 signal peptide.

4. The expression vector of claim 2, wherein the signal peptide sequence fused to the nucleotide base sequence is an IGF-1 signal peptide.

5. A formulation comprising the vector of claim 1 and a pharmaceutically or veterinarily acceptable carrier, vehicle or excipient.

6. A formulation comprising the vector of claim 2 and a pharmaceutically or veterinarily acceptable carrier, vehicle or excipient.

7. The formulation of claim 5, wherein the carrier, vehicle or excipient facilitates transfection and/or improves preservation of the vector or protein.

8. The formulation of claim 6, wherein the carrier, vehicle or excipient facilitates transfection and/or improves preservation of the vector or protein.

9. The vector of claim 1 wherein the polynucleotide has at least 96% identity to SEQ ID NO:3.

10. The vector of claim 1 wherein the polynucleotide has at least 98% identity to SEQ ID NO:3.

11. The vector of claim 1 wherein the polynucleotide has at least 98% identity to SEQ ID NO:3.

12. The vector of claim 1 wherein the polynucleotide has the nucleic acid sequence set forth in SEQ ID NO:3.

13. The vector of claim 1 wherein the canine proGHRH N-terminus deleted polypeptide has at least 98% identity to amino acids 31 to 106 of SEQ ID NO:1.

14. The vector of claim 1 wherein the canine proGHRH N-terminus deleted polypeptide has the sequence set forth in amino acids 31 to 106 of SEQ ID NO:1.

15. The vector of claim 2 wherein the polynucleotide has at least 99% identity to SEQ ID NO:4.

16. The vector of claim 2 wherein the polynucleotide has the nucleic acid sequence set forth in SEQ ID NO:4.

17. The vector of claim 2 wherein the canine mature GHRH polypeptide has at least 97% identity to SEQ ID NO:2.

18. The vector of claim 2 wherein the canine mature GHRH polypeptide has at least 98% identity to SEQ ID NO:2.

19. The vector of claim 2 wherein the canine mature GHRH polypeptide has the sequence as set forth in SEQ ID NO:2.

20. An expression vector for expressing a canine pro-GHRH comprising a polynucleotide operatively linked to a promoter and optionally to an enhancer, wherein the polynucleotide comprises
  (a) a polynucleotide encoding a canine proGHRH polypeptide having at least 95% sequence identity to amino acids 21 to 106 of SEQ ID NO: 1; or
  (b) a polynucleotide having at least 95% sequence identity to nucleotides 61 to 321 of SEQ ID NO: 3 and encoding a canine proGHRH; and
  (c) a polynucleotide encoding a secretory signal peptide sequence fused to the nucleotide base sequence from nucleotide 61 to nucleotide 321 of SEQ ID NO: 3;
  wherein the canine pro-GHRH polypeptide, when expressed in vivo in a canine is able to be cellularly processed to mature canine GHRH with the ability to stimulate growth hormone secretion.

* * * * *

SEQUENCE LISTING

<160> NUMBER OF SEQ ID NOS: 51

<210> SEQ ID NO 1
<211> LENGTH: 106
<212> TYPE: PRT
<213> ORGANISM: Canis familiaris

<400> SEQUENCE: 1

Met Pro Leu Trp Val Phe Phe Leu Val Ile Leu Thr Leu Ser Ser Gly
 1               5                  10                  15

Ser His Ser Ser Pro Pro Ser Leu Pro Ile Arg Ile Pro Arg Tyr Ala
            20                  25                  30

Asp Ala Ile Phe Thr Asn Ser Tyr Arg Lys Val Leu Gly Gln Leu Ser
        35                  40                  45

Ala Arg Lys Leu Leu Gln Asp Ile Met Ser Arg Gln Gln Gly Glu Arg
    50                  55                  60

Asn Arg Glu Gln Gly Ala Lys Val Arg Leu Gly Arg Gln Val Asp Ser
65                  70                  75                  80

Leu Trp Ala Ser Gln Lys Gln Met Ala Leu Glu Asn Ile Leu Ala Ser
                85                  90                  95

Leu Leu Gln Lys Arg Arg Asn Ser Gln Gly
            100                 105

<210> SEQ ID NO 2
<211> LENGTH: 45
<212> TYPE: PRT
<213> ORGANISM: Canis familiaris
<220> FEATURE:
<221> NAME/KEY: MISC_FEATURE
<222> LOCATION: (1)
<223> OTHER INFORMATION: may or may not be present
<220> FEATURE:
<223> OTHER INFORMATION: c-term may or may not be amidated; see
      specification as filed for detailed description of preferred
      embodiments

<400> SEQUENCE: 2

Met Tyr Ala Asp Ala Ile Phe Thr Asn Ser Tyr Arg Lys Val Leu Gly
 1               5                  10                  15

Gln Leu Ser Ala Arg Lys Leu Leu Gln Asp Ile Met Ser Arg Gln Gln
            20                  25                  30

Gly Glu Arg Asn Arg Glu Gln Gly Ala Lys Val Arg Leu
        35                  40                  45

<210> SEQ ID NO 3
<211> LENGTH: 321
<212> TYPE: DNA
<213> ORGANISM: Canis familiaris

<400> SEQUENCE: 3
atgccactct gggtgttctt cctggtgatc ctcaccctca gcagtggctc ccactcttcc      60
ccgccatccc tgcccatcag aatccctcgg tatgcagacg ccatcttcac caacagctac     120
cggaaggtgc tgggccagct gtccgcccgc aagctcctgc aggacatcat gagccggcag     180
cagggagaga gaaaccggga gcaaggagca aaggtacgac tcggccgtca ggtggacagt     240
ctgtgggcaa gccaaaagca gatggcattg gagaacatcc tggcatccct gttacagaaa     300
cgcaggaact cccaaggatg a                                                321

<210> SEQ ID NO 4
<211> LENGTH: 132
<212> TYPE: DNA
<213> ORGANISM: Canis familiaris

<400> SEQUENCE: 4
tatgcagacg ccatcttcac caacagctac cggaaggtgc tgggccagct gtccgcccgc      60
aagctcctgc aggacatcat gagccggcag cagggagaga gaaaccggga gcaaggagca     120
aaggtacgac tc                                                         132

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 5
atgcyrctct gggtgytc                                                    18

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 6
tcatccytgg gagttcc                                                     17

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 7
gctaccggaa ggtkctgggc c                                                21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 8
ggcccagmac cttccggtag c                                                21

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aagcagtggt atcaacgcag agtacgcggg                                       30

<210> SEQ ID NO 10
<211> LENGTH: 45
<212> TYPE: DNA
<213> ORGANISM: Artificial Sequence

```
<220> FEATURE:
<223> OTHER INFORMATION: Description of Artificial Sequence: Primer

<400> SEQUENCE: 10
ctaatacgac tcactatagg gcaagcagtg gtatcaacgc agagt            45

<210> SEQ ID NO 11
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (57)
<223> OTHER INFORMATION: a, t, c or g

<400> SEQUENCE: 11
aagcagtggt atcaacgcag agtactttttt tttttttttt tttttttttt tttttvn   57

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Probe

<400> SEQUENCE: 12
gccatcttca cyaacarcta ccggaaggtb ctgggccagc tvtcygcccg           50

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 13
tttcgcggat cctatgcaga cgccatcttc acc                            33

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 14
aaagctctag atcaacggcc gagtcgtacc tttgc                          35

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 15
gatctgcagc acgtgtctag aggatatcga attcgcggcc                     40

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Primer
```

<400> SEQUENCE: 16
gatccgcggc cgcgaattcg atatcctcta gacacgtgct                40

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 17
aaagctctag atcatccttg ggagttcctg                30

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 18
tttacgcgtc gacatgctgc tctgggtgtt c                31

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 19
ccgtcgtcga cagagctgag                20

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 20
aaaagcgctg ggcgaaacga agac                24

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 21
aaagccggca tggatttcct ggctgggcga acgaagact gc                42

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 22
tttggttccc cgccatccct g                21

<210> SEQ ID NO 23

-continued

```
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 23
tttaggcctc catccctgcc catc                                              24

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 24
tttgtatacg cagacgccat cttcacc                                           27

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 25
aaagctctag atcagagtcg tacctttgct cc                                     32

<210> SEQ ID NO 26
<211> LENGTH: 321
<212> TYPE: DNA
<213> ORGANISM: Artificial Sequence
<220> FEATURE:
<223> OTHER INFORMATION: Description of Artificial Sequence: Synthetic
      construct pNB209
<220> FEATURE:
<221> NAME/KEY: CDS
<222> LOCATION: (1)..(318)

<400> SEQUENCE: 26 atg ctg ctc tgg gtg ttc ttc ctg gtg atc ctc acc ctc agc agt ggc         48
Met Leu Leu Trp Val Phe Phe Leu Val Ile Leu Thr Leu Ser Ser Gly
 1               5                  10                  15 tcc cac tct tcc ccg cca tcc ctg ccc atc aga atc cct cgg tat gca         96
Ser His Ser Ser Pro Pro Ser Leu Pro Ile Arg Ile Pro Arg Tyr Ala
            20                  25                  30 gac gcc atc ttc acc aac agc tac cgg aag gtg ctg ggc cag ctg tcc        144
Asp Ala Ile Phe Thr Asn Ser Tyr Arg Lys Val Leu Gly Gln Leu Ser
        35                  40                  45 gcc cgc aag ctc ctg cag gac atc atg agc cgg cag cag gga gag aga        192
Ala Arg Lys Leu Leu Gln Asp Ile Met Ser Arg Gln Gln Gly Glu Arg
    50                  55                  60 aac cgg gag caa gga gca aag gta cga ctc ggc cgt cag gtg gac agt        240
Asn Arg Glu Gln Gly Ala Lys Val Arg Leu Gly Arg Gln Val Asp Ser
65                  70                  75                  80 ctg tgg gca agc caa aag cag atg gca ttg gag aac atc ctg gca tcc        288
Leu Trp Ala Ser Gln Lys Gln Met Ala Leu Glu Asn Ile Leu Ala Ser
                85                  90                  95 ctg tta cag aaa cgc agg aac tcc caa gga tga                            321
Leu Leu Gln Lys Arg Arg Asn Ser Gln Gly
            100                 105

<210> SEQ ID NO 27
<211> LENGTH: 106
```

<212> TYPE: PRT
<213> ORGANISM: Artificial Sequence
<220> FEATURE:
<223> OTHER INFORMATION: Description of Artificial Sequence: Synthetic
      construct pNB209

<400> SEQUENCE: 27

Met Leu Leu Trp Val Phe Phe Leu Val Ile Leu Thr Leu Ser Ser Gly
1               5                   10                  15

Ser His Ser Ser Pro Pro Ser Leu Pro Ile Arg Ile Pro Arg Tyr Ala
            20                  25                  30

Asp Ala Ile Phe Thr Asn Ser Tyr Arg Lys Val Leu Gly Gln Leu Ser
        35                  40                  45

Ala Arg Lys Leu Leu Gln Asp Ile Met Ser Arg Gln Gln Gly Glu Arg
    50                  55                  60

Asn Arg Glu Gln Gly Ala Lys Val Arg Leu Gly Arg Gln Val Asp Ser
65                  70                  75                  80

Leu Trp Ala Ser Gln Lys Gln Met Ala Leu Glu Asn Ile Leu Ala Ser
                85                  90                  95

Leu Leu Gln Lys Arg Arg Asn Ser Gln Gly
            100                 105

<210> SEQ ID NO 28
<211> LENGTH: 333
<212> TYPE: DNA
<213> ORGANISM: Artificial Sequence
<220> FEATURE:
<223> OTHER INFORMATION: Description of Artificial Sequence: Synthetic
      construct pNB210
<220> FEATURE:
<221> NAME/KEY: CDS
<222> LOCATION: (1)..(330)

<400> SEQUENCE: 28 atg gat gca atg aag aga ggg ctc tgc tgt gtg ctg ctg ctg tgt gga    48
Met Asp Ala Met Lys Arg Gly Leu Cys Cys Val Leu Leu Leu Cys Gly
1               5                   10                  15 gca gtc ttc gtt tcg ccc agc tcc ccg cca tcc ctg ccc atc aga atc    96
Ala Val Phe Val Ser Pro Ser Ser Pro Pro Ser Leu Pro Ile Arg Ile
            20                  25                  30 cct cgg tat gca gac gcc atc ttc acc aac agc tac cgg aag gtg ctg   144
Pro Arg Tyr Ala Asp Ala Ile Phe Thr Asn Ser Tyr Arg Lys Val Leu
        35                  40                  45 ggc cag ctg tcc gcc cgc aag ctc ctg cag gac atc atg agc cgg cag   192
Gly Gln Leu Ser Ala Arg Lys Leu Leu Gln Asp Ile Met Ser Arg Gln
    50                  55                  60 cag gga gag aga aac cgg gag caa gga gca aag gta cga ctc ggc cgt   240
Gln Gly Glu Arg Asn Arg Glu Gln Gly Ala Lys Val Arg Leu Gly Arg
65                  70                  75                  80 cag gtg gac agt ctg tgg gca agc caa aag cag atg gca ttg gag aac   288
Gln Val Asp Ser Leu Trp Ala Ser Gln Lys Gln Met Ala Leu Glu Asn
                85                  90                  95 atc ctg gca tcc ctg tta cag aaa cgc agg aac tcc caa gga tga       333
Ile Leu Ala Ser Leu Leu Gln Lys Arg Arg Asn Ser Gln Gly
            100                 105                 110

<210> SEQ ID NO 29
<211> LENGTH: 110
<212> TYPE: PRT
<213> ORGANISM: Artificial Sequence
<220> FEATURE:
<223> OTHER INFORMATION: Description of Artificial Sequence: Synthetic
      construct pNB210

<400> SEQUENCE: 29

```
Met Asp Ala Met Lys Arg Gly Leu Cys Cys Val Leu Leu Leu Cys Gly
1               5                   10                  15

Ala Val Phe Val Ser Pro Ser Pro Pro Ser Leu Pro Ile Arg Ile
            20                  25                  30

Pro Arg Tyr Ala Asp Ala Ile Phe Thr Asn Ser Tyr Arg Lys Val Leu
        35                  40                  45

Gly Gln Leu Ser Ala Arg Lys Leu Leu Gln Asp Ile Met Ser Arg Gln
    50                  55                  60

Gln Gly Glu Arg Asn Arg Glu Gln Gly Ala Lys Val Arg Leu Gly Arg
65              70                  75                  80

Gln Val Asp Ser Leu Trp Ala Ser Gln Lys Gln Met Ala Leu Glu Asn
            85                  90                  95

Ile Leu Ala Ser Leu Leu Gln Lys Arg Arg Asn Ser Gln Gly
        100                 105                 110
```

<210> SEQ ID NO 30
<211> LENGTH: 330
<212> TYPE: DNA
<213> ORGANISM: Artificial Sequence
<220> FEATURE:
<223> OTHER INFORMATION: Description of Artificial Sequence: Synthetic
      construct pNB211
<220> FEATURE:
<221> NAME/KEY: CDS
<222> LOCATION: (1)..(327)

<400> SEQUENCE: 30

```
atg gat gca atg aag aga ggg ctc tgc tgt gtg ctg ctg ctg tgt gga     48
Met Asp Ala Met Lys Arg Gly Leu Cys Cys Val Leu Leu Leu Cys Gly
1               5                   10                  15 gca gtc ttc gtt tcg ccc agc cct cca tcc ctg ccc atc aga atc cct     96
Ala Val Phe Val Ser Pro Ser Pro Pro Ser Leu Pro Ile Arg Ile Pro
            20                  25                  30 cgg tat gca gac gcc atc ttc acc aac agc tac cgg aag gtg ctg ggc    144
Arg Tyr Ala Asp Ala Ile Phe Thr Asn Ser Tyr Arg Lys Val Leu Gly
        35                  40                  45 cag ctg tcc gcc cgc aag ctc ctg cag gac atc atg agc cgg cag cag    192
Gln Leu Ser Ala Arg Lys Leu Leu Gln Asp Ile Met Ser Arg Gln Gln
    50                  55                  60 gga gag aga aac cgg gag caa gga gca aag gta cga ctc ggc cgt cag    240
Gly Glu Arg Asn Arg Glu Gln Gly Ala Lys Val Arg Leu Gly Arg Gln
65              70                  75                  80 gtg gac agt ctg tgg gca agc caa aag cag atg gca ttg gag aac atc    288
Val Asp Ser Leu Trp Ala Ser Gln Lys Gln Met Ala Leu Glu Asn Ile
            85                  90                  95 ctg gca tcc ctg tta cag aaa cgc agg aac tcc caa gga tga            330
Leu Ala Ser Leu Leu Gln Lys Arg Arg Asn Ser Gln Gly
        100                 105
```

<210> SEQ ID NO 31
<211> LENGTH: 109
<212> TYPE: PRT
<213> ORGANISM: Artificial Sequence
<220> FEATURE:
<223> OTHER INFORMATION: Description of Artificial Sequence: Synthetic
      construct pNB211

<400> SEQUENCE: 31

```
Met Asp Ala Met Lys Arg Gly Leu Cys Cys Val Leu Leu Leu Cys Gly
1               5                   10                  15
```

```
Ala Val Phe Val Ser Pro Ser Pro Ser Leu Pro Ile Arg Ile Pro
            20                  25                  30

Arg Tyr Ala Asp Ala Ile Phe Thr Asn Ser Tyr Arg Lys Val Leu Gly
        35                  40                  45

Gln Leu Ser Ala Arg Lys Leu Leu Gln Asp Ile Met Ser Arg Gln Gln
    50                  55                  60

Gly Glu Arg Asn Arg Glu Gln Gly Ala Lys Val Arg Leu Gly Arg Gln
65                  70                  75                  80

Val Asp Ser Leu Trp Ala Ser Gln Lys Gln Met Ala Leu Glu Asn Ile
                85                  90                  95

Leu Ala Ser Leu Leu Gln Lys Arg Arg Asn Ser Gln Gly
            100                 105
```

<210> SEQ ID NO 32
<211> LENGTH: 348
<212> TYPE: DNA
<213> ORGANISM: Artificial Sequence
<220> FEATURE:
<223> OTHER INFORMATION: Description of Artificial Sequence: Synthetic construct pNB212
<220> FEATURE:
<221> NAME/KEY: CDS
<222> LOCATION: (1)..(345)

<400> SEQUENCE: 32

```
atg gat gca atg aag aga ggg ctc tgc tgt gtg ctg ctg ctg tgt gga     48
Met Asp Ala Met Lys Arg Gly Leu Cys Cys Val Leu Leu Leu Cys Gly
1               5                   10                  15 gca gtc ttc gtt tcg ccc agc cag gaa atc cat gcc tcc ccg cca tcc     96
Ala Val Phe Val Ser Pro Ser Gln Glu Ile His Ala Ser Pro Pro Ser
            20                  25                  30 ctg ccc atc aga atc cct cgg tat gca gac gcc atc ttc acc aac agc    144
Leu Pro Ile Arg Ile Pro Arg Tyr Ala Asp Ala Ile Phe Thr Asn Ser
        35                  40                  45 tac cgg aag gtg ctg ggc cag ctg tcc gcc cgc aag ctc ctg cag gac    192
Tyr Arg Lys Val Leu Gly Gln Leu Ser Ala Arg Lys Leu Leu Gln Asp
    50                  55                  60 atc atg agc cgg cag cag gga gag aga aac cgg gag caa gga gca aag    240
Ile Met Ser Arg Gln Gln Gly Glu Arg Asn Arg Glu Gln Gly Ala Lys
65                  70                  75                  80 gta cga ctc ggc cgt cag gtg gac agt ctg tgg gca agc caa aag cag    288
Val Arg Leu Gly Arg Gln Val Asp Ser Leu Trp Ala Ser Gln Lys Gln
                85                  90                  95 atg gca ttg gag aac atc ctg gca tcc ctg tta cag aaa cgc agg aac    336
Met Ala Leu Glu Asn Ile Leu Ala Ser Leu Leu Gln Lys Arg Arg Asn
            100                 105                 110 tcc caa gga tga                                                    348
Ser Gln Gly
        115
```

<210> SEQ ID NO 33
<211> LENGTH: 115
<212> TYPE: PRT
<213> ORGANISM: Artificial Sequence
<220> FEATURE:
<223> OTHER INFORMATION: Description of Artificial Sequence: Synthetic construct pNB212

<400> SEQUENCE: 33

```
Met Asp Ala Met Lys Arg Gly Leu Cys Cys Val Leu Leu Leu Cys Gly
1               5                   10                  15
```

```
Ala Val Phe Val Ser Pro Ser Gln Glu Ile His Ala Ser Pro Pro Ser
             20                  25                  30

Leu Pro Ile Arg Ile Pro Arg Tyr Ala Asp Ala Ile Phe Thr Asn Ser
         35                  40                  45

Tyr Arg Lys Val Leu Gly Gln Leu Ser Ala Arg Lys Leu Leu Gln Asp
     50                  55                  60

Ile Met Ser Arg Gln Gln Gly Glu Arg Asn Arg Glu Gln Gly Ala Lys
 65                  70                  75                  80

Val Arg Leu Gly Arg Gln Val Asp Ser Leu Trp Ala Ser Gln Lys Gln
                 85                  90                  95

Met Ala Leu Glu Asn Ile Leu Ala Ser Leu Leu Gln Lys Arg Arg Asn
             100                 105                 110

Ser Gln Gly
        115

<210> SEQ ID NO 34
<211> LENGTH: 345
<212> TYPE: DNA
<213> ORGANISM: Artificial Sequence
<220> FEATURE:
<223> OTHER INFORMATION: Description of Artificial Sequence: Synthetic
      construct pNB213
<220> FEATURE:
<221> NAME/KEY: CDS
<222> LOCATION: (1)..(342)

<400> SEQUENCE: 34 atg gat gca atg aag aga ggg ctc tgc tgt gtg ctg ctg ctg tgt gga        48
Met Asp Ala Met Lys Arg Gly Leu Cys Cys Val Leu Leu Leu Cys Gly
 1               5                  10                  15 gca gtc ttc gtt tcg ccc agc cag gaa atc cat gcc cct cca tcc ctg        96
Ala Val Phe Val Ser Pro Ser Gln Glu Ile His Ala Pro Pro Ser Leu
             20                  25                  30 ccc atc aga atc cct cgg tat gca gac gcc atc ttc acc aac agc tac       144
Pro Ile Arg Ile Pro Arg Tyr Ala Asp Ala Ile Phe Thr Asn Ser Tyr
         35                  40                  45 cgg aag gtg ctg ggc cag ctg tcc gcc cgc aag ctc ctg cag gac atc       192
Arg Lys Val Leu Gly Gln Leu Ser Ala Arg Lys Leu Leu Gln Asp Ile
     50                  55                  60 atg agc cgg cag cag gga gag aga aac cgg gag caa gga gca aag gta       240
Met Ser Arg Gln Gln Gly Glu Arg Asn Arg Glu Gln Gly Ala Lys Val
 65                  70                  75                  80 cga ctc ggc cgt cag gtg gac agt ctg tgg gca agc caa aag cag atg       288
Arg Leu Gly Arg Gln Val Asp Ser Leu Trp Ala Ser Gln Lys Gln Met
                 85                  90                  95 gca ttg gag aac atc ctg gca tcc ctg tta cag aaa cgc agg aac tcc       336
Ala Leu Glu Asn Ile Leu Ala Ser Leu Leu Gln Lys Arg Arg Asn Ser
             100                 105                 110 caa gga tga                                                            345
Gln Gly <210> SEQ ID NO 35
<211> LENGTH: 114
<212> TYPE: PRT
<213> ORGANISM: Artificial Sequence
<220> FEATURE:
<223> OTHER INFORMATION: Description of Artificial Sequence: Synthetic
      construct pNB213

<400> SEQUENCE: 35

Met Asp Ala Met Lys Arg Gly Leu Cys Cys Val Leu Leu Leu Cys Gly
 1               5                  10                  15
```

```
Ala Val Phe Val Ser Pro Ser Gln Glu Ile His Ala Pro Ser Leu
            20                  25                  30

Pro Ile Arg Ile Pro Arg Tyr Ala Asp Ala Ile Phe Thr Asn Ser Tyr
        35                  40                  45

Arg Lys Val Leu Gly Gln Leu Ser Ala Arg Lys Leu Leu Gln Asp Ile
     50                  55                  60

Met Ser Arg Gln Gln Gly Glu Arg Asn Arg Glu Gln Gly Ala Lys Val
 65                  70                  75                  80

Arg Leu Gly Arg Gln Val Asp Ser Leu Trp Ala Ser Gln Lys Gln Met
             85                  90                  95

Ala Leu Glu Asn Ile Leu Ala Ser Leu Leu Gln Lys Arg Arg Asn Ser
            100                 105                 110

Gln Gly
```

<210> SEQ ID NO 36
<211> LENGTH: 204
<212> TYPE: DNA
<213> ORGANISM: Artificial Sequence
<220> FEATURE:
<223> OTHER INFORMATION: Description of Artificial Sequence: Synthetic construct pNB214
<220> FEATURE:
<221> NAME/KEY: CDS
<222> LOCATION: (1)..(201)

<400> SEQUENCE: 36

```
atg gat gca atg aag aga ggg ctc tgc tgt gtg ctg ctg ctg tgt gga     48
Met Asp Ala Met Lys Arg Gly Leu Cys Cys Val Leu Leu Leu Cys Gly
 1               5                  10                  15 gca gtc ttc gtt tcg ccc agc tac gca gac gcc atc ttc acc aac agc     96
Ala Val Phe Val Ser Pro Ser Tyr Ala Asp Ala Ile Phe Thr Asn Ser
            20                  25                  30 tac cgg aag gtg ctg ggc cag ctg tcc gcc cgc aag ctc ctg cag gac    144
Tyr Arg Lys Val Leu Gly Gln Leu Ser Ala Arg Lys Leu Leu Gln Asp
        35                  40                  45 atc atg agc cgg cag cag gga gag aga aac cgg gag caa gga gca aag    192
Ile Met Ser Arg Gln Gln Gly Glu Arg Asn Arg Glu Gln Gly Ala Lys
     50                  55                  60 gta cga ctc tga                                                    204
Val Arg Leu
 65
```

<210> SEQ ID NO 37
<211> LENGTH: 67
<212> TYPE: PRT
<213> ORGANISM: Artificial Sequence
<220> FEATURE:
<223> OTHER INFORMATION: Description of Artificial Sequence: Synthetic construct pNB214

<400> SEQUENCE: 37

```
Met Asp Ala Met Lys Arg Gly Leu Cys Cys Val Leu Leu Leu Cys Gly
 1               5                  10                  15

Ala Val Phe Val Ser Pro Ser Tyr Ala Asp Ala Ile Phe Thr Asn Ser
            20                  25                  30

Tyr Arg Lys Val Leu Gly Gln Leu Ser Ala Arg Lys Leu Leu Gln Asp
        35                  40                  45

Ile Met Ser Arg Gln Gln Gly Glu Arg Asn Arg Glu Gln Gly Ala Lys
     50                  55                  60

Val Arg Leu
```

<210> SEQ ID NO 38
<211> LENGTH: 219
<212> TYPE: DNA
<213> ORGANISM: Artificial Sequence
<220> FEATURE:
<223> OTHER INFORMATION: Description of Artificial Sequence: Synthetic construct pNB215
<220> FEATURE:
<221> NAME/KEY: CDS
<222> LOCATION: (1)..(216)

<400> SEQUENCE: 38

```
atg gat gca atg aag aga ggg ctc tgc tgt gtg ctg ctg ctg tgt gga      48
Met Asp Ala Met Lys Arg Gly Leu Cys Cys Val Leu Leu Leu Cys Gly
  1               5                  10                  15 gca gtc ttc gtt tcg ccc agc cag gaa atc cat gcc tac gca gac gcc      96
Ala Val Phe Val Ser Pro Ser Gln Glu Ile His Ala Tyr Ala Asp Ala
             20                  25                  30 atc ttc acc aac agc tac cgg aag gtg ctg ggc cag ctg tcc gcc cgc     144
Ile Phe Thr Asn Ser Tyr Arg Lys Val Leu Gly Gln Leu Ser Ala Arg
         35                  40                  45 aag ctc ctg cag gac atc atg agc cgg cag cag gga gag aga aac cgg     192
Lys Leu Leu Gln Asp Ile Met Ser Arg Gln Gln Gly Glu Arg Asn Arg
     50                  55                  60 gag caa gga gca aag gta cga ctc tga                                 219
Glu Gln Gly Ala Lys Val Arg Leu
 65                  70
```

<210> SEQ ID NO 39
<211> LENGTH: 72
<212> TYPE: PRT
<213> ORGANISM: Artificial Sequence
<220> FEATURE:
<223> OTHER INFORMATION: Description of Artificial Sequence: Synthetic construct pNB215

<400> SEQUENCE: 39

```
Met Asp Ala Met Lys Arg Gly Leu Cys Cys Val Leu Leu Leu Cys Gly
  1               5                  10                  15

Ala Val Phe Val Ser Pro Ser Gln Glu Ile His Ala Tyr Ala Asp Ala
             20                  25                  30

Ile Phe Thr Asn Ser Tyr Arg Lys Val Leu Gly Gln Leu Ser Ala Arg
         35                  40                  45

Lys Leu Leu Gln Asp Ile Met Ser Arg Gln Gln Gly Glu Arg Asn Arg
     50                  55                  60

Glu Gln Gly Ala Lys Val Arg Leu
 65                  70
```

<210> SEQ ID NO 40
<211> LENGTH: 324
<212> TYPE: DNA
<213> ORGANISM: Artificial Sequence
<220> FEATURE:
<223> OTHER INFORMATION: Description of Artificial Sequence: Synthetic construct pNB216
<220> FEATURE:
<221> NAME/KEY: CDS
<222> LOCATION: (1)..(318)

<400> SEQUENCE: 40

```
atg ctg ctg tgg gtg ttc ttc ctg gtg atc ctg acc ctg agc agc ggc      48
Met Leu Leu Trp Val Phe Phe Leu Val Ile Leu Thr Leu Ser Ser Gly
  1               5                  10                  15
```

```
agc cac agc agc ccc ccc agc ctg ccc atc cgc atc ccc cgg tac gcc      96
Ser His Ser Ser Pro Pro Ser Leu Pro Ile Arg Ile Pro Arg Tyr Ala
            20                  25                  30 gac gcc atc ttc acc aac agc tac cgg aaa gtg ctg ggc cag ctg agc     144
Asp Ala Ile Phe Thr Asn Ser Tyr Arg Lys Val Leu Gly Gln Leu Ser
        35                  40                  45 gcc cgg aag ctg ctg cag gac atc atg agc cgc cag cag ggc gag cgc     192
Ala Arg Lys Leu Leu Gln Asp Ile Met Ser Arg Gln Gln Gly Glu Arg
50                  55                  60 aac cgc gag cag ggc gcc aaa gtg cgg ctg ggc cgc caa gtg gac agc     240
Asn Arg Glu Gln Gly Ala Lys Val Arg Leu Gly Arg Gln Val Asp Ser
65                  70                  75                  80 ctg tgg gcc agc cag aaa cag atg gcc ctg gag aac atc ctg gcc agc     288
Leu Trp Ala Ser Gln Lys Gln Met Ala Leu Glu Asn Ile Leu Ala Ser
                85                  90                  95 ctg ctg cag aag cgg cgg aac agc cag ggc tgataa                      324
Leu Leu Gln Lys Arg Arg Asn Ser Gln Gly
            100                 105

<210> SEQ ID NO 41
<211> LENGTH: 333
<212> TYPE: DNA
<213> ORGANISM: Artificial Sequence
<220> FEATURE:
<223> OTHER INFORMATION: Description of Artificial Sequence: Synthetic
      construct pNB217
<220> FEATURE:
<221> NAME/KEY: CDS
<222> LOCATION: (1)..(327)

<400> SEQUENCE: 41 atg gat gca atg aag aga ggg ctc tgc tgt gtg ctg ctg ctg tgt gga      48
Met Asp Ala Met Lys Arg Gly Leu Cys Cys Val Leu Leu Leu Cys Gly
1               5                   10                  15 gca gtc ttc gtt tcg ccc agc ccc ccc agc ctg ccc atc cgc atc ccc      96
Ala Val Phe Val Ser Pro Ser Pro Pro Ser Leu Pro Ile Arg Ile Pro
            20                  25                  30 cgg tac gcc gac gcc atc ttc acc aac agc tac cgg aaa gtg ctg ggc     144
Arg Tyr Ala Asp Ala Ile Phe Thr Asn Ser Tyr Arg Lys Val Leu Gly
        35                  40                  45 cag ctg agc gcc cgg aag ctg ctg cag gac atc atg agc cgc cag cag     192
Gln Leu Ser Ala Arg Lys Leu Leu Gln Asp Ile Met Ser Arg Gln Gln
    50                  55                  60 ggc gag cgc aac cgc gag cag ggc gcc aaa gtg cgg ctg ggc cgc caa     240
Gly Glu Arg Asn Arg Glu Gln Gly Ala Lys Val Arg Leu Gly Arg Gln
65                  70                  75                  80 gtg gac agc ctg tgg gcc agc cag aaa cag atg gcc ctg gag aac atc     288
Val Asp Ser Leu Trp Ala Ser Gln Lys Gln Met Ala Leu Glu Asn Ile
                85                  90                  95 ctg gcc agc ctg ctg cag aag cgg cgg aac agc cag ggc tgataa          333
Leu Ala Ser Leu Leu Gln Lys Arg Arg Asn Ser Gln Gly
            100                 105

<210> SEQ ID NO 42
<211> LENGTH: 348
<212> TYPE: DNA
<213> ORGANISM: Artificial Sequence
<220> FEATURE:
<223> OTHER INFORMATION: Description of Artificial Sequence: Synthetic
      construct pNB218
<220> FEATURE:
<221> NAME/KEY: CDS
<222> LOCATION: (1)..(342)
```

```
<400> SEQUENCE: 42 atg gat gca atg aag aga ggg ctc tgc tgt gtg ctg ctg ctg tgt gga      48
Met Asp Ala Met Lys Arg Gly Leu Cys Cys Val Leu Leu Leu Cys Gly
 1               5                  10                  15 gca gtc ttc gtt tcg ccc agc cag gaa atc cat gcc ccc ccc agc ctg      96
Ala Val Phe Val Ser Pro Ser Gln Glu Ile His Ala Pro Pro Ser Leu
                 20                  25                  30 ccc atc cgc atc ccc cgg tac gcc gac gcc atc ttc acc aac agc tac     144
Pro Ile Arg Ile Pro Arg Tyr Ala Asp Ala Ile Phe Thr Asn Ser Tyr
         35                  40                  45 cgg aaa gtg ctg ggc cag ctg agc gcc cgg aag ctg ctg cag gac atc     192
Arg Lys Val Leu Gly Gln Leu Ser Ala Arg Lys Leu Leu Gln Asp Ile
 50                  55                  60 atg agc cgc cag cag ggc gag cgc aac cgc gag cag ggc gcc aaa gtg     240
Met Ser Arg Gln Gln Gly Glu Arg Asn Arg Glu Gln Gly Ala Lys Val
 65                  70                  75                  80 cgg ctg ggc cgc caa gtg gac agc ctg tgg gcc agc cag aaa cag atg     288
Arg Leu Gly Arg Gln Val Asp Ser Leu Trp Ala Ser Gln Lys Gln Met
                 85                  90                  95 gcc ctg gag aac atc ctg gcc agc ctg ctg cag aag cgg cgg aac agc     336
Ala Leu Glu Asn Ile Leu Ala Ser Leu Leu Gln Lys Arg Arg Asn Ser
            100                 105                 110 cag ggc tgataa                                                      348
Gln Gly

<210> SEQ ID NO 43
<211> LENGTH: 204
<212> TYPE: DNA
<213> ORGANISM: Artificial Sequence
<220> FEATURE:
<223> OTHER INFORMATION: Description of Artificial Sequence: Synthetic
      construct pNB219
<220> FEATURE:
<221> NAME/KEY: CDS
<222> LOCATION: (1)..(201)

<400> SEQUENCE: 43 atg gat gca atg aag aga ggg ctc tgc tgt gtg ctg ctg ctg tgt gga      48
Met Asp Ala Met Lys Arg Gly Leu Cys Cys Val Leu Leu Leu Cys Gly
 1               5                  10                  15 gca gtc ttc gtt tcg ccc agc tac gcc gac gcc atc ttc acc aac agc      96
Ala Val Phe Val Ser Pro Ser Tyr Ala Asp Ala Ile Phe Thr Asn Ser
                 20                  25                  30 tac cgg aaa gtg ctg ggc cag ctg agc gcc cgg aag ctg ctg cag gac     144
Tyr Arg Lys Val Leu Gly Gln Leu Ser Ala Arg Lys Leu Leu Gln Asp
         35                  40                  45 atc atg agc cgc cag cag ggc gag cgc aac cgc gag cag ggc gcc aaa     192
Ile Met Ser Arg Gln Gln Gly Glu Arg Asn Arg Glu Gln Gly Ala Lys
 50                  55                  60 gtg cgg ctg tga                                                     204
Val Arg Leu
 65

<210> SEQ ID NO 44
<211> LENGTH: 219
<212> TYPE: DNA
<213> ORGANISM: Artificial Sequence
<220> FEATURE:
<223> OTHER INFORMATION: Description of Artificial Sequence: Synthetic
      construct pNB220
<220> FEATURE:
<221> NAME/KEY: CDS
<222> LOCATION: (1)..(216)
```

-continued

```
<400> SEQUENCE: 44 atg gat gca atg aag aga ggg ctc tgc tgt gtg ctg ctg ctg tgt gga    48
Met Asp Ala Met Lys Arg Gly Leu Cys Cys Val Leu Leu Leu Cys Gly
  1               5                  10                  15 gca gtc ttc gtt tcg ccc agc cag gaa atc cat gcc tac gcc gac gcc    96
Ala Val Phe Val Ser Pro Ser Gln Glu Ile His Ala Tyr Ala Asp Ala
             20                  25                  30 atc ttc acc aac agc tac cgg aaa gtg ctg ggc cag ctg agc gcc cgg   144
Ile Phe Thr Asn Ser Tyr Arg Lys Val Leu Gly Gln Leu Ser Ala Arg
         35                  40                  45 aag ctg ctg cag gac atc atg agc cgc cag cag ggc gag cgc aac cgc   192
Lys Leu Leu Gln Asp Ile Met Ser Arg Gln Gln Gly Glu Arg Asn Arg
     50                  55                  60 gag cag ggc gcc aaa gtg cgg ctg tga                                219
Glu Gln Gly Ala Lys Val Arg Leu
 65                  70

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 45
tttggccccc ccagcctgcc catc                                          24

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 46
aaagctctag attatcagcc ctggctgttc cgc                                33

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 47
tttgtatacg ccgacgccat cttcacc                                       27

<210> SEQ ID NO 48
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 48
aaagctctag atcacagccg cactttggcg cc                                 32

<210> SEQ ID NO 49
<211> LENGTH: 222
<212> TYPE: DNA
<213> ORGANISM: Artificial Sequence
<220> FEATURE:
<223> OTHER INFORMATION: Description of Artificial Sequence: Synthetic
      construct pNB179
<220> FEATURE:
```

```
<221> NAME/KEY: CDS
<222> LOCATION: (1)..(219)

<400> SEQUENCE: 49 atg gat gca atg aag aga ggg ctc tgc tgt gtg ctg ctg ctg tgt gga      48
Met Asp Ala Met Lys Arg Gly Leu Cys Cys Val Leu Leu Leu Cys Gly
 1               5                  10                  15 gca gtc ttc gtt tcg ccc agc ggt acc gga tcc tat gca gac gcc atc      96
Ala Val Phe Val Ser Pro Ser Gly Thr Gly Ser Tyr Ala Asp Ala Ile
                20                  25                  30 ttc acc aac agc tac cgg aag gtg ctg ggc cag ctg tcc gcc cgc aag     144
Phe Thr Asn Ser Tyr Arg Lys Val Leu Gly Gln Leu Ser Ala Arg Lys
            35                  40                  45 ctc ctg cag gac atc atg agc cgg cag cag gga gag aga aac cgg gag     192
Leu Leu Gln Asp Ile Met Ser Arg Gln Gln Gly Glu Arg Asn Arg Glu
        50                  55                  60 caa gga gca aag gta cga ctc ggc cgt tga                             222
Gln Gly Ala Lys Val Arg Leu Gly Arg
    65                  70

<210> SEQ ID NO 50
<211> LENGTH: 73
<212> TYPE: PRT
<213> ORGANISM: Artificial Sequence
<220> FEATURE:
<223> OTHER INFORMATION: Description of Artificial Sequence: Synthetic
      construct pNB179

<400> SEQUENCE: 50

Met Asp Ala Met Lys Arg Gly Leu Cys Cys Val Leu Leu Leu Cys Gly
 1               5                  10                  15

Ala Val Phe Val Ser Pro Ser Gly Thr Gly Ser Tyr Ala Asp Ala Ile
                20                  25                  30

Phe Thr Asn Ser Tyr Arg Lys Val Leu Gly Gln Leu Ser Ala Arg Lys
            35                  40                  45

Leu Leu Gln Asp Ile Met Ser Arg Gln Gln Gly Glu Arg Asn Arg Glu
        50                  55                  60

Gln Gly Ala Lys Val Arg Leu Gly Arg
    65                  70

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (27)
<223> OTHER INFORMATION: a, t, c or g

<400> SEQUENCE: 51
tttttttttt tttttttttt tttttvn                                        27
```